United States Patent
Loke et al.

(10) Patent No.: US 11,911,738 B2
(45) Date of Patent: Feb. 27, 2024

(54) SYSTEMS AND METHODS HAVING AN ANALYZER FOR USE IN PREPARING PARTICLES

(71) Applicant: Matralix Pte Ltd, Singapore (SG)

(72) Inventors: Siew Keong Loke, Singapore (SG); Kit Ying Soo, Singapore (SG)

(73) Assignee: MATRALIX PTE LTD, Singapore (SG)

( * ) Notice: Subject to any disclaimer, the term of this patent is extended or adjusted under 35 U.S.C. 154(b) by 0 days.

(21) Appl. No.: 17/899,317

(22) Filed: Aug. 30, 2022

(65) Prior Publication Data

US 2022/0410110 A1 Dec. 29, 2022

Related U.S. Application Data

(60) Division of application No. 16/846,201, filed on Apr. 10, 2020, now Pat. No. 11,491,454, which is a
(Continued)

(51) Int. Cl.
*B01J 13/04* (2006.01)
*A61K 8/11* (2006.01)
(Continued)

(52) U.S. Cl.
CPC ............... *B01J 13/04* (2013.01); *A61K 8/11* (2013.01); *A61K 8/927* (2013.01); *A61Q 19/00* (2013.01);
(Continued)

(58) Field of Classification Search
None
See application file for complete search history.

(56) References Cited

U.S. PATENT DOCUMENTS 2,446,784 A   8/1948   Daley et al.
2,887,724 A   5/1959   Bettes, Jr.
(Continued)

FOREIGN PATENT DOCUMENTS

FR   2336176 A1   7/1977
JP   H11-509768 A   8/1999
(Continued)

OTHER PUBLICATIONS

EP Office Action dated Jun. 19, 2023 as received in Application No. 18817027.8.
(Continued)

*Primary Examiner* — Jeffrey D Washville
(74) *Attorney, Agent, or Firm* — Maschoff Brennan

(57) ABSTRACT

The system can include: a conduit having a first dimension with an inlet and outlet; an extruder having an inlet and an outlet located within the conduit, an extruder orifice having a second dimension that is smaller than the first dimension; a carrier fluid reservoir coupled with the conduit inlet; an extruder reservoir coupled with the extruder inlet; and a particle collector fluidly coupled with the conduit outlet, wherein the particle collector has a collector inlet with a first temperature and a collector outlet with a second temperature. The method can include flowing carrier fluid through the extrudate conduit; extruding wax with the extruder into the carrier fluid that is flowing through the extrudate conduit such that the extrudate separates into extrudate segments separated from each other by carrier fluid segments; and flowing the extrudate into the particle collector so as to form wax particles.

22 Claims, 23 Drawing Sheets

Related U.S. Application Data continuation of application No. 16/006,474, filed on Jun. 12, 2018, now Pat. No. 10,639,607.

(60) Provisional application No. 62/521,062, filed on Jun. 16, 2017.

(51) Int. Cl.
*A61K 8/92* (2006.01)
*A61Q 19/00* (2006.01)
*C08L 91/06* (2006.01)

(52) U.S. Cl.
CPC .......... *C08L 91/06* (2013.01); *A61K 2800/10* (2013.01); *A61K 2800/412* (2013.01); *C08L 2207/53* (2013.01)

(56) References Cited

U.S. PATENT DOCUMENTS

| | | | |
|---|---|---|---|
| 3,029,466 | A | 4/1962 | Guill |
| 3,092,553 | A | 6/1963 | Fisher, Jr. et al. |
| 3,320,338 | A | 5/1967 | Lemelson |
| 3,329,994 | A | 7/1967 | Watanbe |
| 3,389,194 | A | 6/1968 | Somerville |
| 3,457,336 | A | 7/1969 | Harris |
| 3,468,986 | A | 9/1969 | Watanabe |
| 4,251,195 | A | 2/1981 | Suzuki et al. |
| 4,422,985 | A | 12/1983 | Morishita et al. |
| 4,481,157 | A | 11/1984 | Morishita et al. |
| 5,330,835 | A | 7/1994 | Kikuchi et al. |
| 5,595,757 | A | 1/1997 | Kiefer et al. |
| 5,888,538 | A | 3/1999 | Kiefer et al. |
| 6,251,661 | B1 | 6/2001 | Urabe et al. |
| 7,578,951 | B2 | 8/2009 | Dunfield et al. |
| 8,021,582 | B2 | 9/2011 | Lee et al. |
| 8,114,319 | B2 | 2/2012 | Davis et al. |
| 8,256,091 | B2 | 9/2012 | Duescher |
| 8,348,651 | B2 | 1/2013 | Juan Mata |
| 8,551,763 | B2 | 10/2013 | Fournier-Bidoz et al. |
| 8,663,511 | B2 | 3/2014 | Kim et al. |
| 8,883,864 | B2 | 11/2014 | Higuchi et al. |
| 8,911,788 | B2 | 12/2014 | Ioualalen et al. |
| 9,192,679 | B2 | 11/2015 | Ioualalen et al. |
| 9,510,609 | B2 | 12/2016 | Kamaguchi et al. |
| 2003/0090015 | A1 | 5/2003 | Nakamura et al. |
| 2003/0133538 | A1 | 7/2003 | Herve et al. |
| 2008/0003142 | A1 | 1/2008 | Link et al. |
| 2009/0004337 | A1 | 1/2009 | Liu et al. |
| 2010/0137163 | A1* | 6/2010 | Link ................ B01L 3/502784 506/40 |

FOREIGN PATENT DOCUMENTS

| | | |
|---|---|---|
| TW | 201000616 A1 | 1/2010 |
| WO | 02/43646 A1 | 6/2002 |
| WO | 20030090015 A1 | 5/2003 |
| WO | 2008/146162 A1 | 12/2008 |
| WO | 2008/146162 A8 | 12/2008 |
| WO | 2018/229685 A1 | 12/2018 |

OTHER PUBLICATIONS

International Search Report dated Sep. 17, 2018 as received in Application No. PCT/IB2018/054328.
Written Opinion of the International Searching Authority dated Sep. 17, 2018 as received in Application No. PCT/IB2018/054328.
European Search Report issued in corresponding application No. 18817027.8 dated Dec. 4, 2020.
Japanese Office Action issued in corresponding application No. 2020-519194 dated Jan. 26, 2021.

* cited by examiner

SYSTEMS AND METHODS HAVING AN ANALYZER FOR USE IN PREPARING PARTICLES

CROSS-REFERENCE

This patent application is a divisional of U.S. application Ser. No. 16/846,201 filed Apr. 10, 2020, which is a continuation of U.S. application Ser. No. 16/006,474 filed Jun. 12, 2018, which claims priority to U.S. Provisional Application No. 62/521,062 filed Jun. 16, 2017, which applications are incorporated herein by specific reference in its entirety.

BACKGROUND

Wax is used in a variety of industrial applications. Often, the wax is used in a particle form. As such, the production of wax particles can provide an important aspect of such industrial applications that use wax. It can be favorable in many instances for the wax particles to have mono-dispersity or a common particle size. Wax particles are often produced by extrusion of molten wax through an orifice.

Some wax particle formation techniques include extruding molten wax as a jet of wax particles into air or another (static or moving) fluid. The jet of a wax stream is subject to an instability, which ruptures the stream of wax into small molten wax droplets that solidify into the wax particles. The rupturing can be accomplished by a variety of mechanisms, such as by gravity, electrostatics, shear, or the like. Polydispersity of droplets is an inherent feature of instability-driven jet rupture, and has been well studied for over a hundred years. Such a jet-based approach to forming wax particles is shown in FIG. 1A.

Other wax particle formation techniques include extruding molten wax from an orifice into a liquid that forms drops once the wax stream emits from the orifice. The wax stream is extruded into a bath of liquid, and, depending on the relative density between the two fluids, is directed either downward or upward. The drop, upon reaching a critical size, is detached from the orifice via buoyancy, which acts against gravity and surface tension. In most typical cases, drop size is nearly independent of orifice size below a certain threshold (~2 mm), and it is extremely difficult to produce sub-millimeter wax particles. This is in addition to the fact that the throughput of this method is relatively lower than the jet-based method. Such a drops-based approach to forming wax particles is shown in FIG. 1B.

SUMMARY

In some embodiments, a system for forming wax particles can include: a conduit with a lumen having a first dimension and having an inlet and an outlet; an extruder having an inlet and an extruder orifice as an outlet located within the conduit, the extruder orifice having a second dimension that is smaller than the first dimension; a carrier fluid reservoir fluidly coupled with the conduit inlet; an extruder reservoir fluidly coupled with the extruder inlet; and a particle collector fluidly coupled with the conduit outlet, wherein the particle collector has a collector inlet with a first temperature and a collector outlet with a second temperature that is lower than the first temperature with a temperature gradient between the first temperature and second temperature. In some aspects, the conduit is adapted to be an extrudate conduit that allows for extrudate to flow therein with a carrier fluid. In some aspects, the ratio of the second dimension to the first dimension is about 1:2 to 1:20, or 1:5 to 1:15, or 1:8 to 1:12, or 1:10. In some aspects, the extruder and conduit cooperate to form an orifice contactor. In some aspects, a heating system is included that has one or more heaters thermally coupled with at least the carrier fluid reservoir, extruder reservoir, and particle collector. In some aspects, a heater is included that is thermally coupled with the extruder reservoir. In some aspects, a cooling system is included that has one or more coolers thermally coupled with an outlet end of the particle collector. In some aspects, a control system is included that has a computer processor adapted to control the system. In some aspects, a pump is included that is operatively coupled with the extruder reservoir. In some aspects, the extruder reservoir is adapted as a wax reservoir. In some aspects, one or more thermocouples are included that are operatively coupled with the wax reservoir. In some aspects, one or more pressure sensors are included that are operatively coupled with the wax reservoir. In some aspects, the wax reservoir is configured as a mixer. In some aspects, a wax dispenser controller is adapted to control a wax pump and wax heater and receive data from a wax pressure sensor, wax thermocouple, and wax flowrate sensor. In some aspects, a heater thermally is included that is coupled with the carrier fluid reservoir. In some aspects, a pump is included that is operatively coupled with the carrier fluid reservoir. In some aspects, one or more thermocouples are included that are operatively coupled with the carrier fluid reservoir. In some aspects, one or more pressure sensors are included that are operatively coupled with the carrier fluid reservoir. In some aspects, a carrier fluid dispenser controller is included that is adapted to control a carrier fluid pump and carrier fluid heater and receive data from a carrier fluid pressure sensor, carrier fluid thermocouple, and carrier fluid flowrate sensor. In some aspects, the particle collector includes the extrudate conduit coupled to a particle collector inlet. In some aspects, the particle collector includes a fluid column that is vertically oriented. In some aspects, the particle collector includes a particle selector. In some aspects, the particle collector includes a particle selector that has a rotating arm. In some aspects, a waste chamber is included at an outlet of the particle collector. In some aspects, a product chamber is included at an outlet of the particle collector. In some aspects, a heater is included at an inlet side of the particle collector. In some aspects, a cooler is included at an outlet side of the particle collector. In some aspects, a particle analyzer is included that is operatively coupled with the particle collector so as to be capable of analyzing particles. In some aspects, the particle analyzer includes a camera. In some aspects, the particle analyzer is operatively coupled with the control system. In some aspects, a particle collector is included that can have at least one of a pressure sensor, flowrate sensor, or thermocouple. In some aspects, the components are contained within a housing, and thereby the system may be configured as a device.

In one embodiment, a method of forming wax particles can include: providing the system or device of one of the embodiments; flowing carrier fluid through the extrudate conduit; extruding wax with the extruder into the carrier fluid that is flowing through the extrudate conduit such that the extrudate separates into extrudate segments separated from each other by carrier fluid segments; and flowing the extrudate into the particle collector so as to form wax particles. In one aspect, the wax particles are wax beads. In one aspect, the method can include heating the wax in the wax reservoir to a temperature above the melting point of the wax. In one aspect, the method can include heating the carrier fluid in the carrier fluid reservoir to a temperature above the melting point of the wax. In one aspect, the method can include adjusting the flowrate of the carrier fluid and flow rate of the extruded wax within the extrudate conduit to control the particle size of the formed wax particles. In one aspect, the method can include cooling an outlet end of the particle collector to a temperature below the wax melting point. In one aspect, the method can include solidifying the wax into wax beads in the particle collector. In one aspect, the method can include activating the particle selector to select wax particles as products. In one aspect, the method can include activating the particle selector to send defective wax particles to waste. In one aspect, the method can include receiving data regarding operation of the system in the control system, and causing a change in the operation of the system.

The foregoing summary is illustrative only and is not intended to be in any way limiting. In addition to the illustrative aspects, embodiments, and features described above, further aspects, embodiments, and features will become apparent by reference to the drawings and the following detailed description.

BRIEF DESCRIPTION OF THE FIGURES

The foregoing and following information as well as other features of this disclosure will become more fully apparent from the following description and appended claims, taken in conjunction with the accompanying drawings. Understanding that these drawings depict only several embodiments in accordance with the disclosure and are, therefore, not to be considered limiting of its scope, the disclosure will be described with additional specificity and detail through use of the accompanying drawings.

Figure 1A:
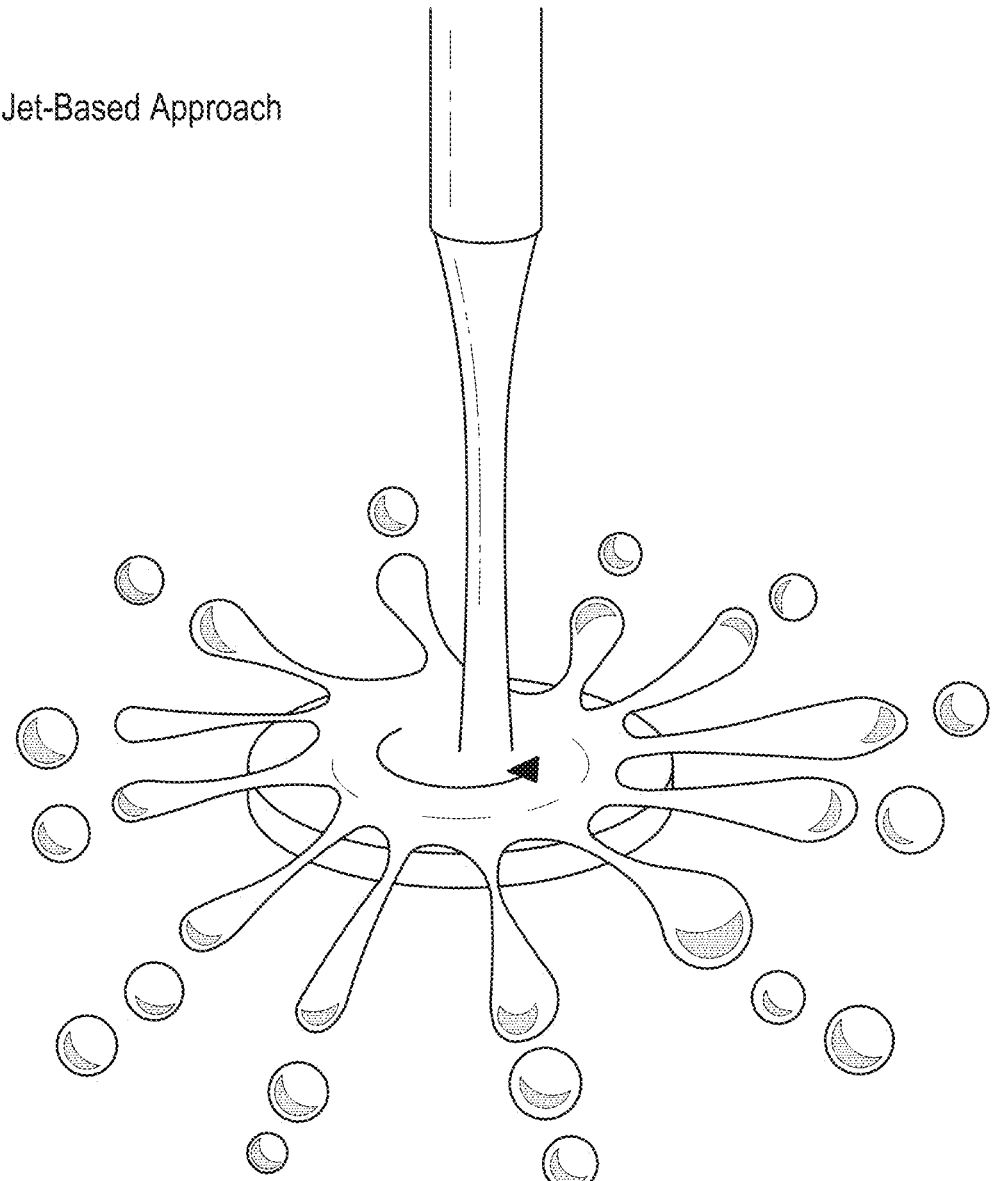
FIG. 1A shows a jet-based approach for forming particles known in the prior art.
Figure 1B:
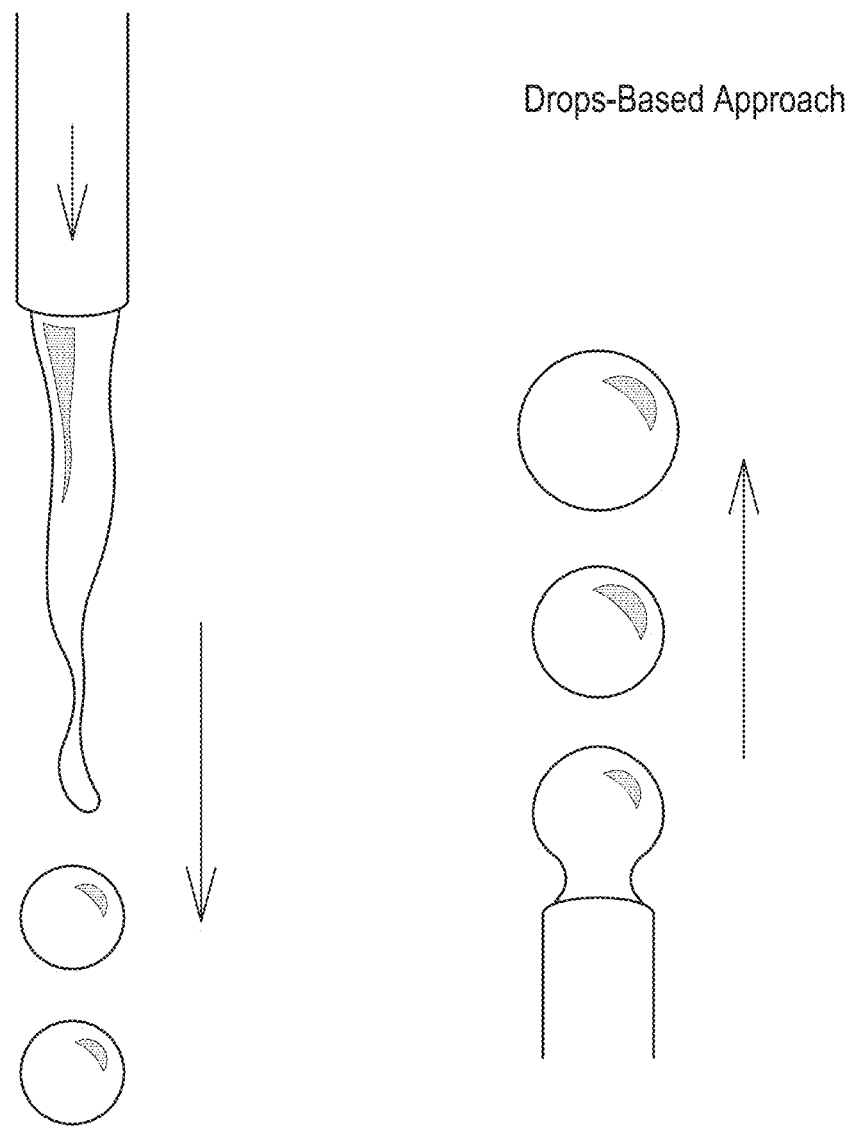
FIG. 1B shows a drops-based approach for forming particles known in the prior art.

The elements shown in the figures are arranged in accordance with at least one of the embodiments described herein, and which arrangement may be modified in accordance with the disclosure provided herein by one of ordinary skill in the art.

DETAILED DESCRIPTION

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented herein. It will be readily understood that the aspects of the present disclosure, as generally described herein, and illustrated in the figures, can be arranged, substituted, combined, separated, and designed in a wide variety of different configurations, all of which are explicitly contemplated herein.

Generally, the present technology relates to systems and methods and can be used to produce wax particles with greater control over particle size and allows for a narrower polydispersity and realization of better mono-dispersity of the wax particles. The system can extrude molten wax in a manner that causes formation of relatively monodisperse particles or a very narrow polydispersity. The method of operating the system can utilize novel physics provided by the design of the system in order to achieve the wax particles.

While the technology is described in connection to wax particles, the systems and methods may also apply to lipid particles and lipid/wax combination particles. The technology may also be used for making hydrophobic particles that include various hydrophobic materials. As such, the descriptions of the systems and methods described herein may be applied to prepare wax particles, lipid particles, lipid/wax particles, hydrophobic particles or combinations thereof. In one aspect, the systems and methods described herein may be applied only to wax particles. In one aspect, the systems and methods described herein may be applied only to lipid particles. In one aspect, the systems and methods described herein may be applied only to lipid/wax combination particles.

In one embodiment, molten wax is extruded from an orifice having a first cross-sectional profile with corresponding first cross-sectional profile dimensions into an immiscible fluid (e.g., immiscible to molten wax) that is within a lumen of a fluid passageway that has a second cross-sectional profile with corresponding second cross-sectional profile dimensions. The first cross-sectional profile and second cross-sectional profile may have the same shape or different shapes. The particle size can be selected based on various factors, such as flow rate of the immiscible fluid, temperature of the immiscible fluid, and relationship of the first cross-sectional profile dimensions to the second cross-sectional profile dimensions, among other factors.

In an example, a flow of molten wax is continually pumped and extruded through an extrusion orifice so that the molten wax is extruded from the orifice in co-flow with another immiscible fluid within a fluid passageway. The extrusion of molten wax into the immiscible fluid forms a train of fast-moving, monodisperse molten wax drops within the fluid passageway. The fluid passageway includes an outlet that is fluidly coupled with a liquid bath of the immiscible fluid. The wax particles form and solidify during transit from the extrusion orifice through the fluid passageway into the liquid bath. The temperature of the molten wax and temperature of the immiscible fluid can form a temperature gradient from the extrusion orifice to and through the fluid passageway, and optionally in the liquid bath, which facilitates the formation and solidification of the wax particles. The wax drops are formed serially and are highly monodisperse. The bead size of the wax particles is ultimately limited by the size of the channels used, which can be as small as 0.1 mm or as large as desired. The extrusion orifice may be considered to be a contactor that contacts the molten wax during extrusion into the immiscible fluid, and thereby may be considered to be an extrusion contactor. The lumen that defines the fluid passageway may also be considered to be a contactor that may contact the molten wax after extrusion during the formation of particles, and thereby may be considered to be a particle contactor.

Figure 2A:
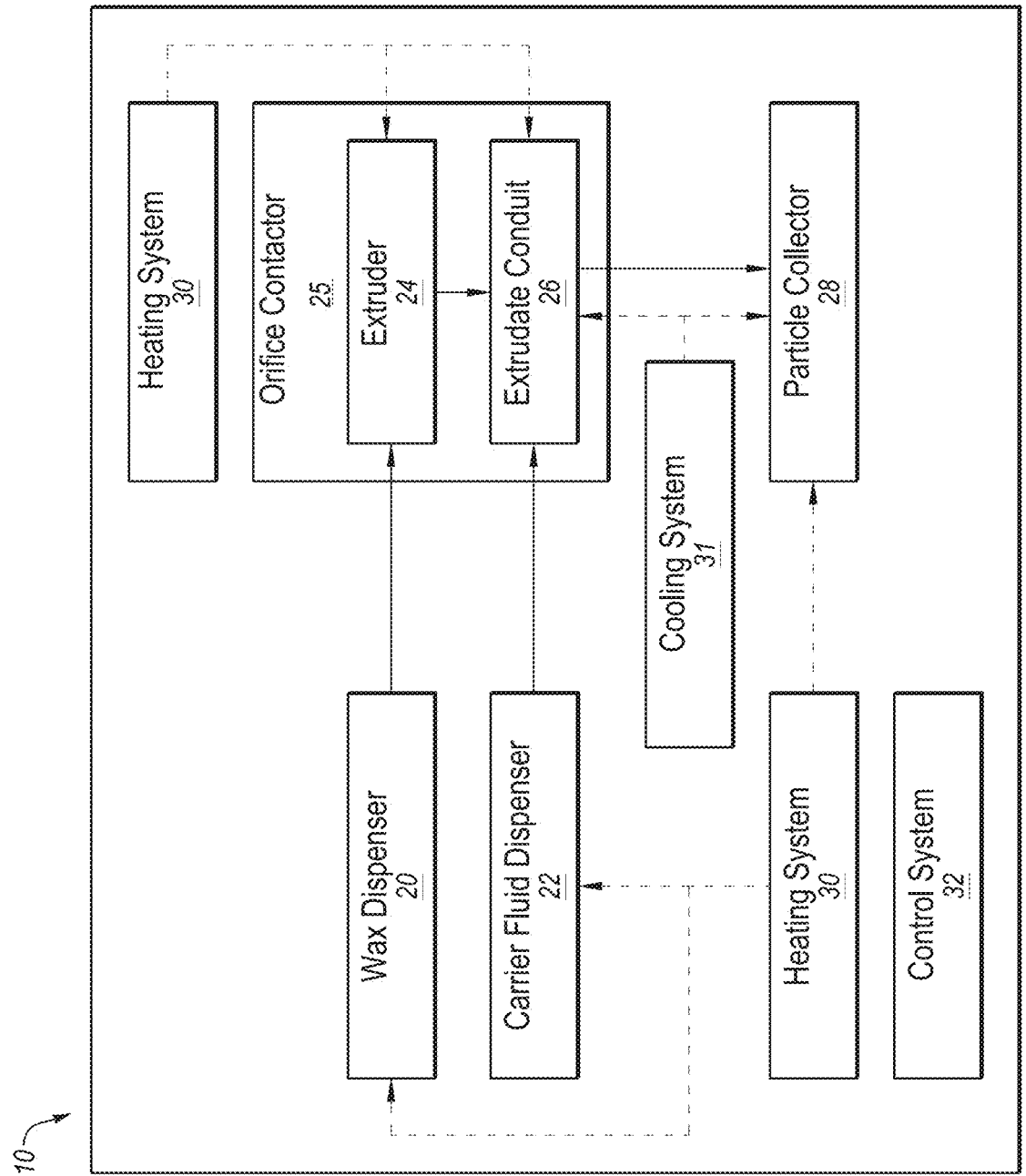
FIG. 2A shows a schematic representation of an embodiment of a particle forming system.

In one embodiment, as shown in FIG. 2A, a system 10 for forming the wax particles with the methodologies described herein can include the following components: wax dispensing unit 20 (e.g., wax dispenser); carrier fluid unit 22 (e.g., carrier fluid dispenser); orifice contactor 25 (e.g., extruder 24 and extrudate conduit 26 combination); collection unit 28 (e.g., particle collector); a heating unit 30 (e.g., heater, heating system); a cooling system 31; and control system 32 (e.g., computer). In FIG. 2A, solid arrows show material flow and dashed arrows show heat flow or cooling flow. As shown, the wax dispenser 20 provides molten wax to the extruder 24 while the carrier fluid dispenser 22 provides carrier fluid to the extrudate conduit 26, where the molten wax and carrier fluid cooperate within the extrudate conduit 26 to form the wax particles. The wax particles are then transferred to the particle collector 28. During the process of forming the wax particles, the heating system 30 can provide heat, independently to the wax dispenser 20, carrier fluid dispenser 22, extruder 24, extrudate conduit 26, and optionally the particle collector 28, as well as any of the conduits between these components that are used for material transfer. The control system 32 can be connected to the components and pumps or other equipment that cooperate with these components in order to control the process to form wax particles of a desired size. These components are described in more detail herein.

Figure 2B:
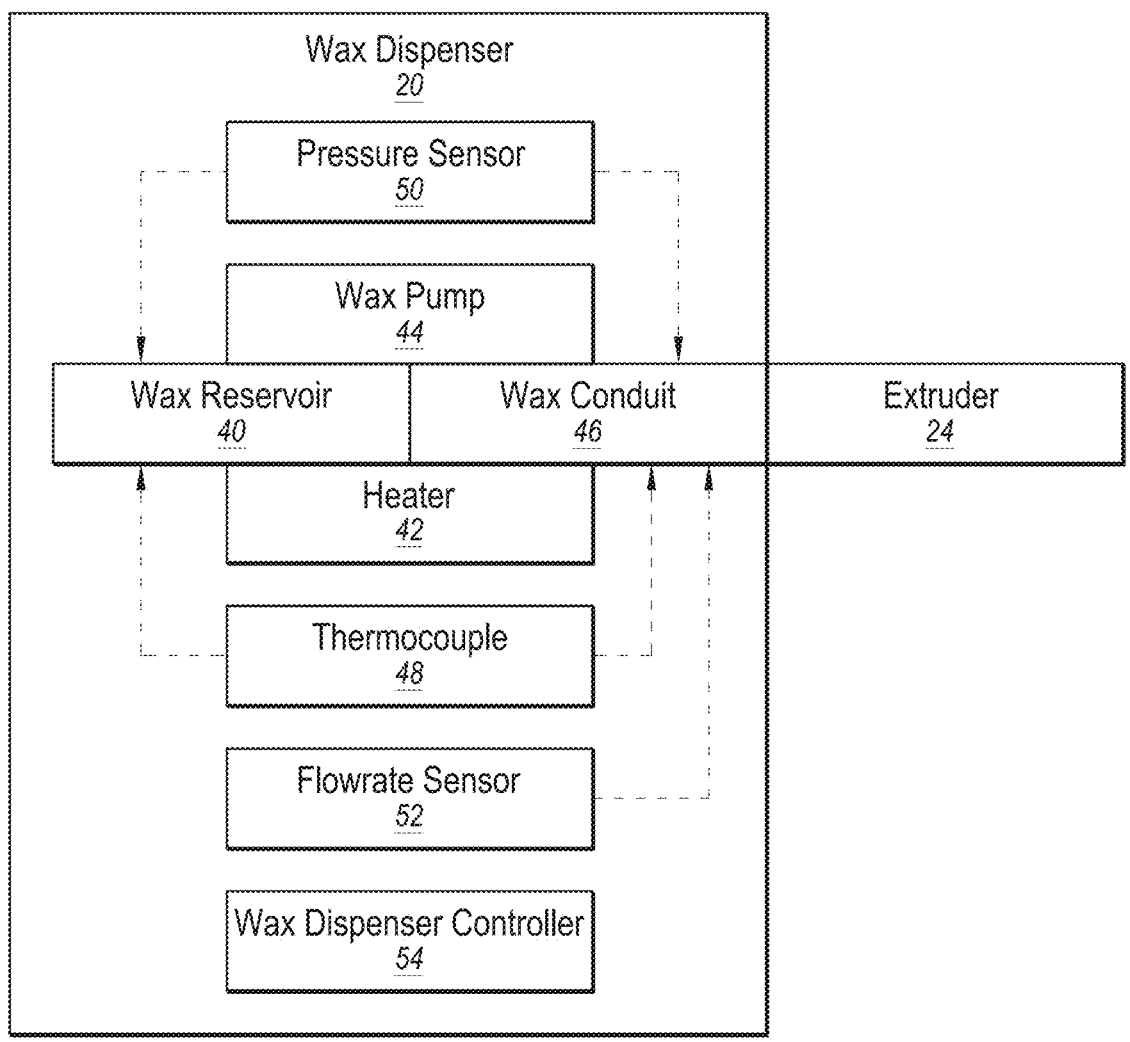
FIG. 2B shows a schematic representation of an embodiment of a wax dispenser.

The wax dispenser 20 can be present in various configurations. In one aspect shown in FIG. 2B, the wax dispenser 20 can include a wax reservoir 40, which can contain solid and/or molten wax. A heater 42 can be associated (e.g., physically coupled or thermally coupled) with the wax reservoir 40 in order to heat the wax to a temperature above the melting point in order to form the molten wax. A wax pump 44 can be associated (e.g., physically coupled or pressure coupled) with the wax reservoir 40 in order to increase the pressure within the wax reservoir 40 and/or operate so as to cause the molten wax to be dispensed from the wax reservoir 40 into a wax conduit 46. It should be recognized that the wax pump 44, or additional wax pumps 44 (e.g., a series of wax pumps 44) can be operatively coupled with the wax conduit 46 to effect wax flow there through. It should also be recognized that the heater 42 may be operatively coupled with the wax conduit 46 to maintain the wax therein as molten wax that may flow there through. Thermocouples 48 (e.g., one or more) and pressure sensors 50 (e.g., one or more) may be located in any location of the wax reservoir 40 and wax conduit 46 so that the temperature and pressure can be monitored. Also, a flowrate sensor 52 may be operatively coupled to the wax conduit 46 so that the flowrate of molten wax may be monitored. A wax dispenser controller 54, which may be part of the control system 32 (FIG. 2A), can be operatively coupled with the heater 42, wax pump 44, thermocouple 48, pressure sensor 50, and/or flowrate sensor 52 so that parameters can be measured and analyzed by the wax dispenser controller 54 so that operating instructions can be provided so that the molten wax is at a desired temperature and pressure and flowing through the wax conduit 46 at a desired flowrate.

In an example of a wax dispenser 20, the temperature and flowrate can be controlled so that the flow of molten wax is pressure driven (e.g. syringe pump) through a fluid routing system (e.g., fluid pathways) that allows the flow of molten wax to and through an extruder 24. Solid wax is loaded into the wax reservoir 40, which is heated to melt the wax to its molten state. Optionally, molten wax can be loaded into the wax reservoir 40 and heat supplied by the heater 42 can maintain the wax at the desired molten state at a desired temperature. In a specific example, the wax reservoir 40 can retain up to 100 mL of wax. Depending on the size of the wax particles, the rate of delivery of the wax can vary from microliters/min to milliliters/min.

In one embodiment, any type of wax (e.g., synthetic and natural), lipids or blends of these materials can be used. Optionally, other hydrophobic materials can be used to prepare hydrophobic particles, such as hydrophobic polymers. Waxes are a diverse class of organic compounds that are hydrophobic, malleable solids near ambient temperatures. Waxes typically have melting points above 40° C. and melt to give low viscosity liquids. A lipid composition can have a typical melting point above about 30° C., which can be applied to suppository compositions. Waxes are insoluble in water, but soluble in most organic, nonpolar solvents. In one aspect, both synthetic waxes and natural waxes (e.g., sourced from animal, vegetable and minerals) can be used. Examples of natural waxes include, but are not limited to, beeswax, carnauba, candelilla, castor, lanolin, ozokerite, shellac, sunflower, rice bran, berry, vegetable, their blends (e.g., combinations), as well as others. Synthetic waxes include, but are not limited to, paraffin, cetyl ester, microcrystalline wax, and lipids including Compritol®, Precirol®, Gelucire®, suppository excipients etc.

Figure 2C:
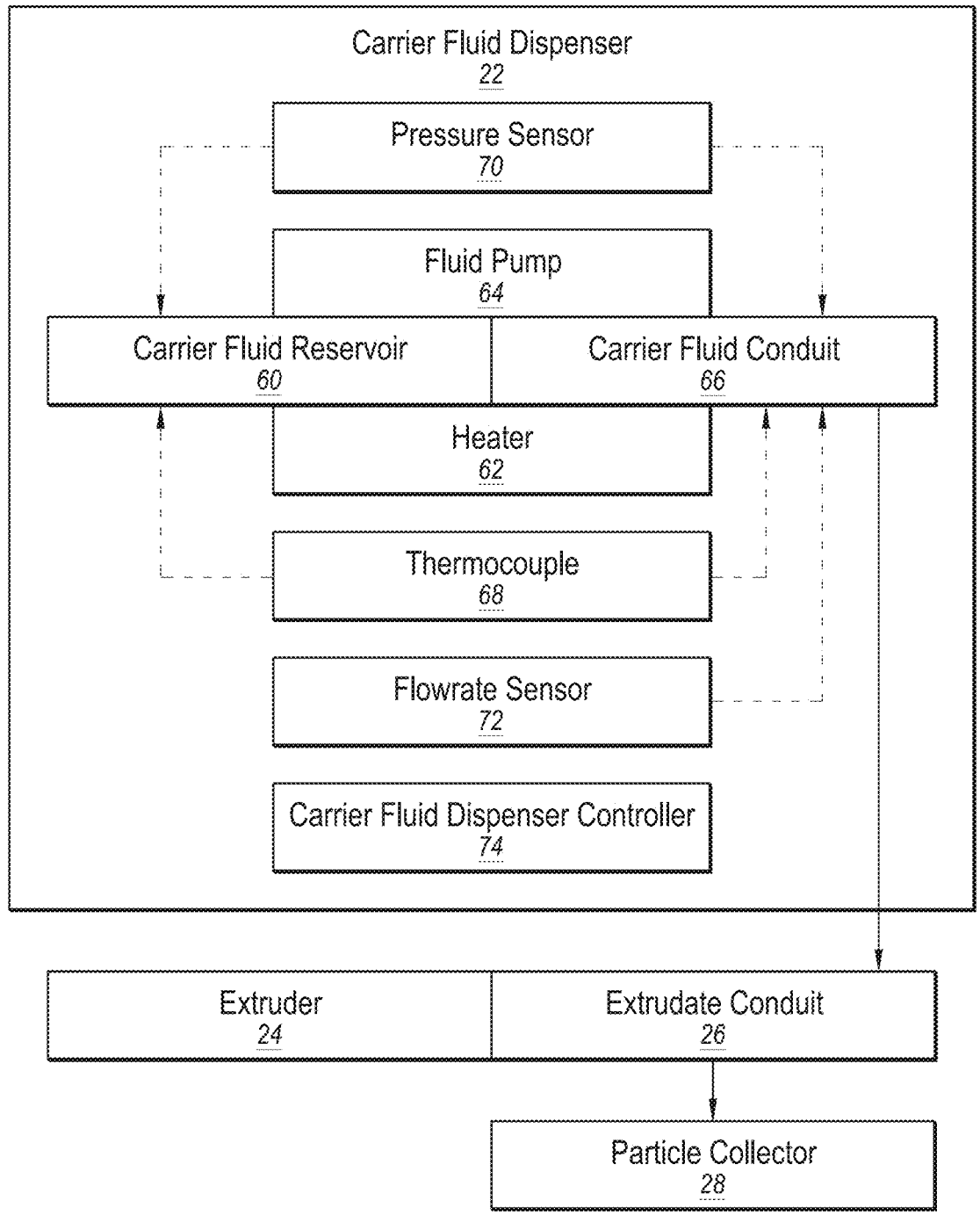
FIG. 2C shows a schematic representation of a carrier fluid dispenser.

The carrier fluid dispenser 22 can be present in various configurations. In one aspect shown in FIG. 2C, the carrier fluid dispenser 22 can include a carrier fluid reservoir 60, which can contain the carrier fluid (e.g., immiscible with molten wax). A heater 62 can be associated (e.g., physically coupled or thermally coupled) with the carrier fluid reservoir 60 in order to heat the carrier fluid to a temperature below, equal to or above the melting point of the molten wax, where the temperature can vary for desired results. A fluid pump 64 can be associated (e.g., physically coupled or pressure coupled) with the carrier fluid reservoir 60 in order to increase the pressure within the carrier fluid reservoir 60 and/or operate so as to cause the carrier fluid to be dispensed from the carrier fluid reservoir 60 into a carrier fluid conduit 66. It should be recognized that the fluid pump 64, or additional pumps 64 (e.g., a series of pumps 64) can be operatively coupled with the carrier fluid conduit 66 to effect carrier fluid flow therethrough. It should also be recognized that the heater 62 may be operatively coupled with the carrier fluid conduit 66 to maintain the temperature of the carrier fluid that may flow therethrough. Thermocouples 68 (e.g., one or more) and pressure sensors 70 (e.g., one or more) may be located in any location of the carrier fluid reservoir 60 and carrier fluid conduit 66 so that the temperature and pressure of the carrier fluid can be monitored. Also, a flowrate sensor 72 may be operatively coupled to the carrier fluid conduit 66 so that the flowrate of carrier fluid may be monitored. A carrier fluid dispenser controller 74, which may be part of the control system 32 (FIG. 2A), can be operatively coupled with the heater 62, fluid pump 64, thermocouple 68, pressure sensor 70, and/or flowrate sensor 72 so that parameters can be measured and analyzed by the carrier fluid dispenser controller 74 so that operating instructions can be provided so that the carrier fluid is at a desired temperature and pressure and flowing through the carrier fluid conduit 66 at a desired flowrate to the extrudate conduit 26.

In one example, the carrier fluid is conditioned to be suitable for carrying the molten wax as it transitions into solid state particles, and then transports the particles to the particle collector. The carrier fluid contacts the molten wax as it is extruded from the extruder and then flows with the molten wax through the extrudate conduit during solidification and particle formation. The relative sizes of the extruder and extrudate conduit along with the relative rates of flows of the molten wax and carrier fluid as well as the temperatures or temperature gradients influence the size of the wax particles that are generated.

The carrier fluid can be any fluid that is immiscible with the wax that is being processed into wax particles. Some examples of carrier fluid include, without limitation, water, silicon oil, glycerine, polyvinyl alcohol solution, combinations thereof, and the like. In some instances, the carrier fluid can have a boiling temperature higher than the melting temperature of the wax, such as preferably at least 5° C., 10° C., 15° C. or 20° C. higher than the melting point of the wax. Before the carrier fluid comes into contact with the molten wax stream, the carrier fluid is heated and maintained at a temperature close to or higher than that of the molten wax to prevent premature solidification of wax upon extrusion and during the flow through the orifice contactor.

The orifice contactor 25 can be present in various configurations and include the extruder 24 and extrudate conduit 26. In one aspect shown in FIGS. 3A and 3B, the orifice contactor 25 includes an extruder 24 and an extrudate conduit 26 containing the extruder orifice 80 (e.g., nozzle) of the extruder 24. The orifice contactor 25 includes an extruder inlet 82 fluidly coupled with the extruder orifice 80, which are parts of the extruder 24. Additionally, the orifice contactor 25 includes the carrier fluid inlet 84 that is connected to the fluid conduit 86, where the fluid conduit contains the extruder 24. The fluid conduit 86 transitions to the extrudate conduit 26 at the extruder orifice 80. However, it should be recognized that the fluid conduit 86 and extrudate conduit 26 may be the same conduit. In operation, the orifice contactor 25 brings the molten stream of wax via the extruder inlet 82 and carrier fluid via the carrier fluid inlet 84 such that the molten stream of wax is extruded from the extruder orifice 80 into the extrudate conduit 26 so that the molten wax and carrier fluid come into contact. Through design of the extruder orifice 80 and choice of appropriate flow rates for the molten wax and the carrier fluid, the molten wax forms wax particles that begin to flow within the carrier fluid down the extrudate conduit 26. As shown, the formation of wax particles within the carrier fluid creates a continuous, serial alternation of wax segments 85 and carrier segments 87 are produced. The sizes of the wax segments 85 and carrier segments 87 can determine the size and shape of the wax particles that are produced. The orifice contactor 25 can range from 10-3000 μm in diameter at the extrudate conduit 26. The orifice contactor 25 can be configured with different extruder orifice 80 dimensions and different extrudate conduit 26 dimensions in order to prepare particles of different size ranges. In one example, the extruder orifice 80 and extrudate conduit 26 dimension ratio can be about 1:2 to 1:20, or 1:5 to 1:15, or 1:8 to 1:12, or 1:10. These wax segments 85 may be in particulate form or cylindrical form; however, it should be recognized that as the wax segments 85 traverse the extrudate conduit 26 toward the particle collector 28 that the wax rolls into particulates that can be spherical.

Figure 3A:
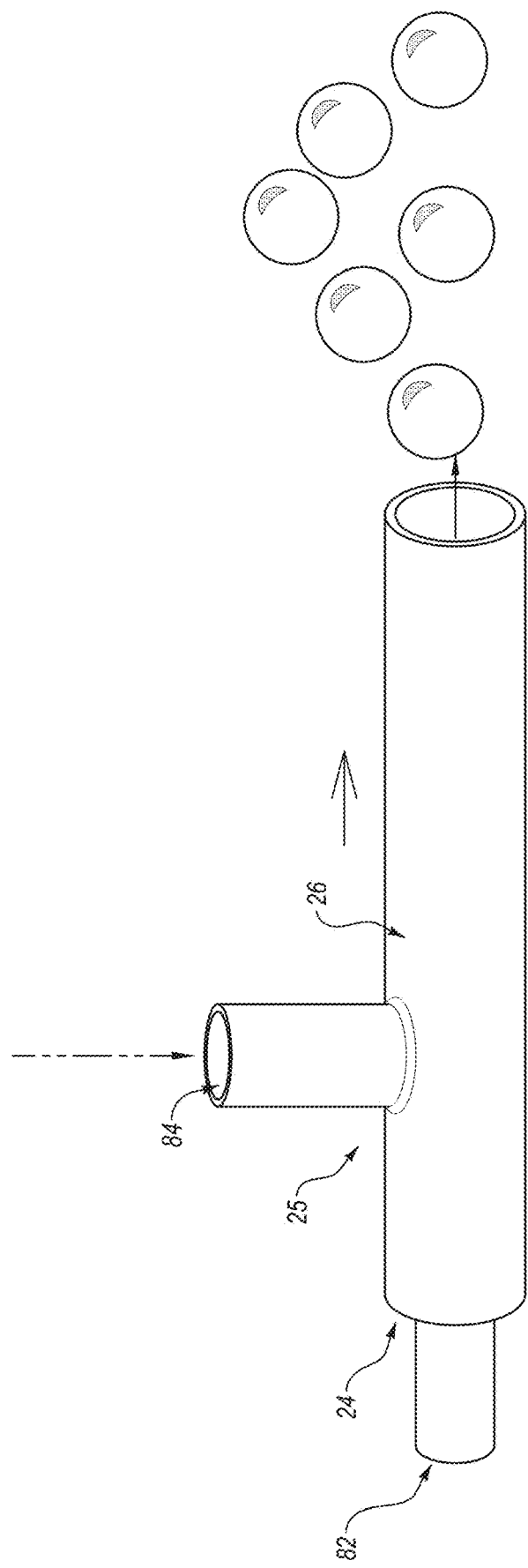
FIG. 3A shows an embodiment of a particle extruding system that extrudes particles into a carrier fluid.
Figure 3B:
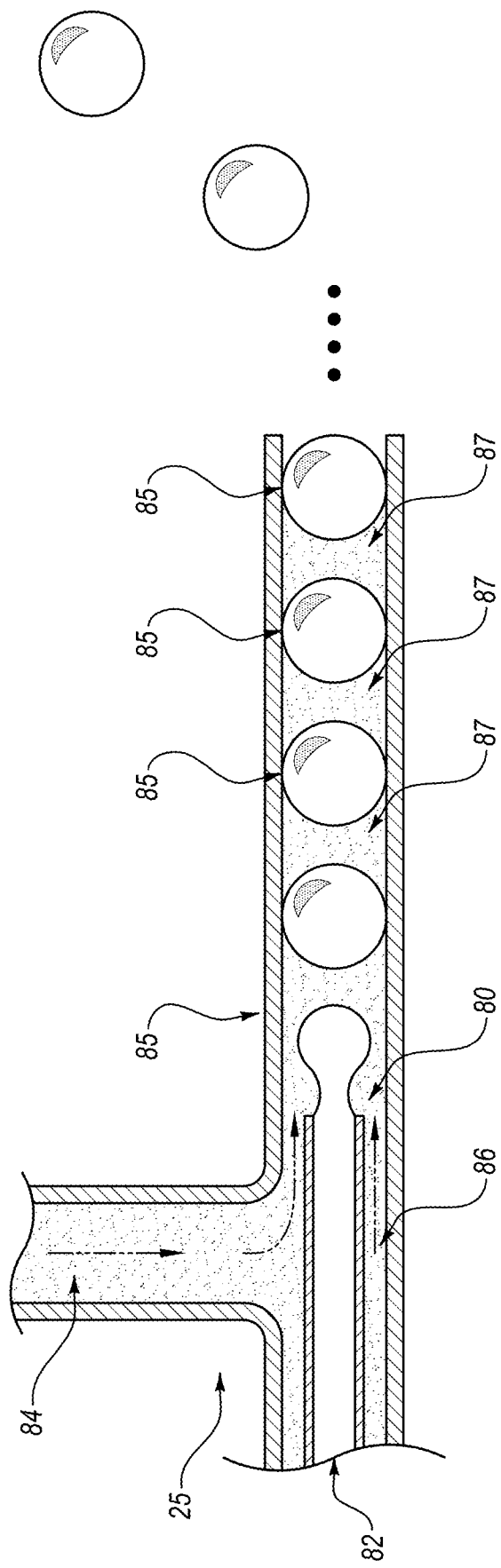
FIG. 3B shows a cross-sectional view of an embodiment of a particle extruding system that extrudes particles into a carrier fluid.

It should be recognized that the orifice contactor 25 can be prepared in various configurations. As shown in FIGS. 3A and 3B, the extruder 24 is a separate member that is inserted into a lumen of the extrudate conduit 26, which are then fastened together to make a fluid tight seal so that the carrier fluid and molten wax can only flow towards the particle collector 28. That is, an extruder tube is inserted into the lumen of the carrier fluid tube past the junction where the carrier fluid inlet 84 is located.

Figure 3C:
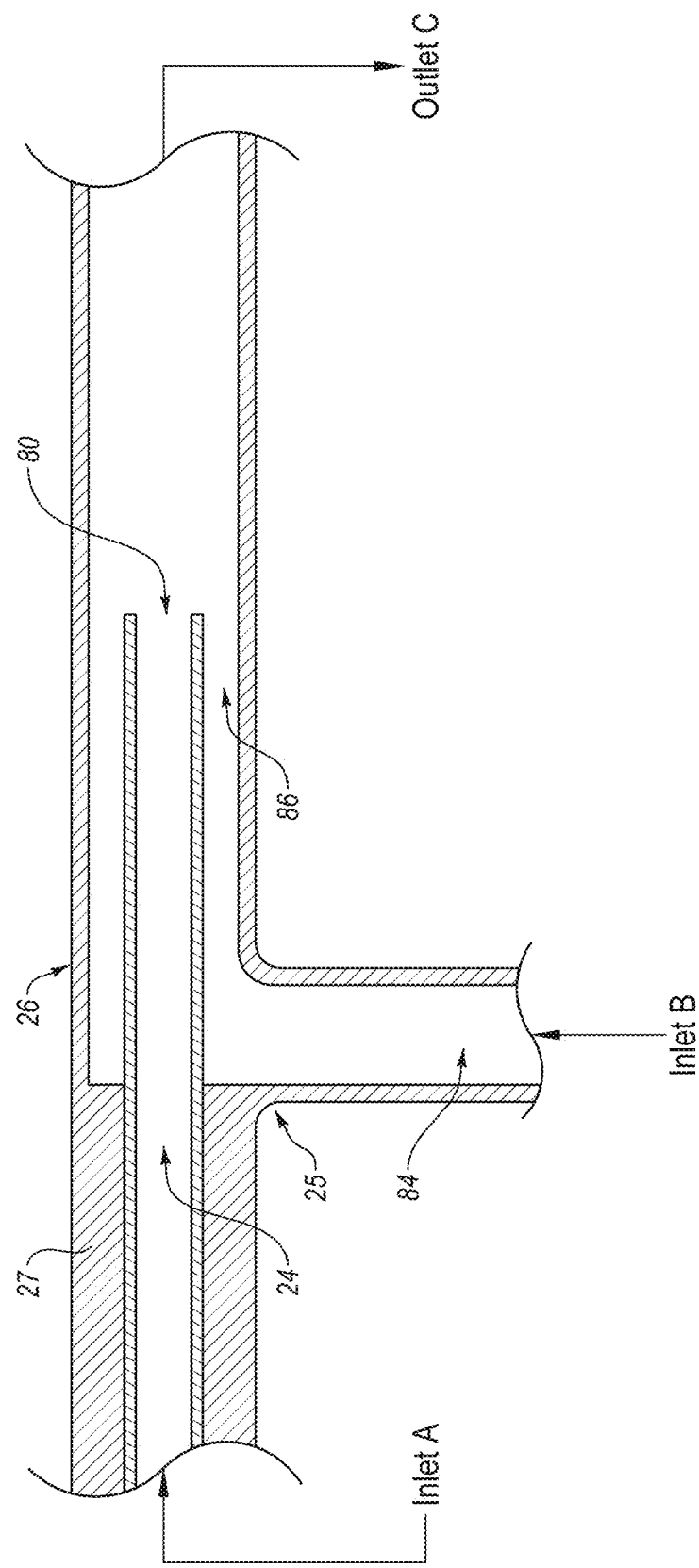
FIG. 3C shows a cross-sectional view of an embodiment of a particle extruding system that extrudes particles into a carrier fluid.
Figure 3D:
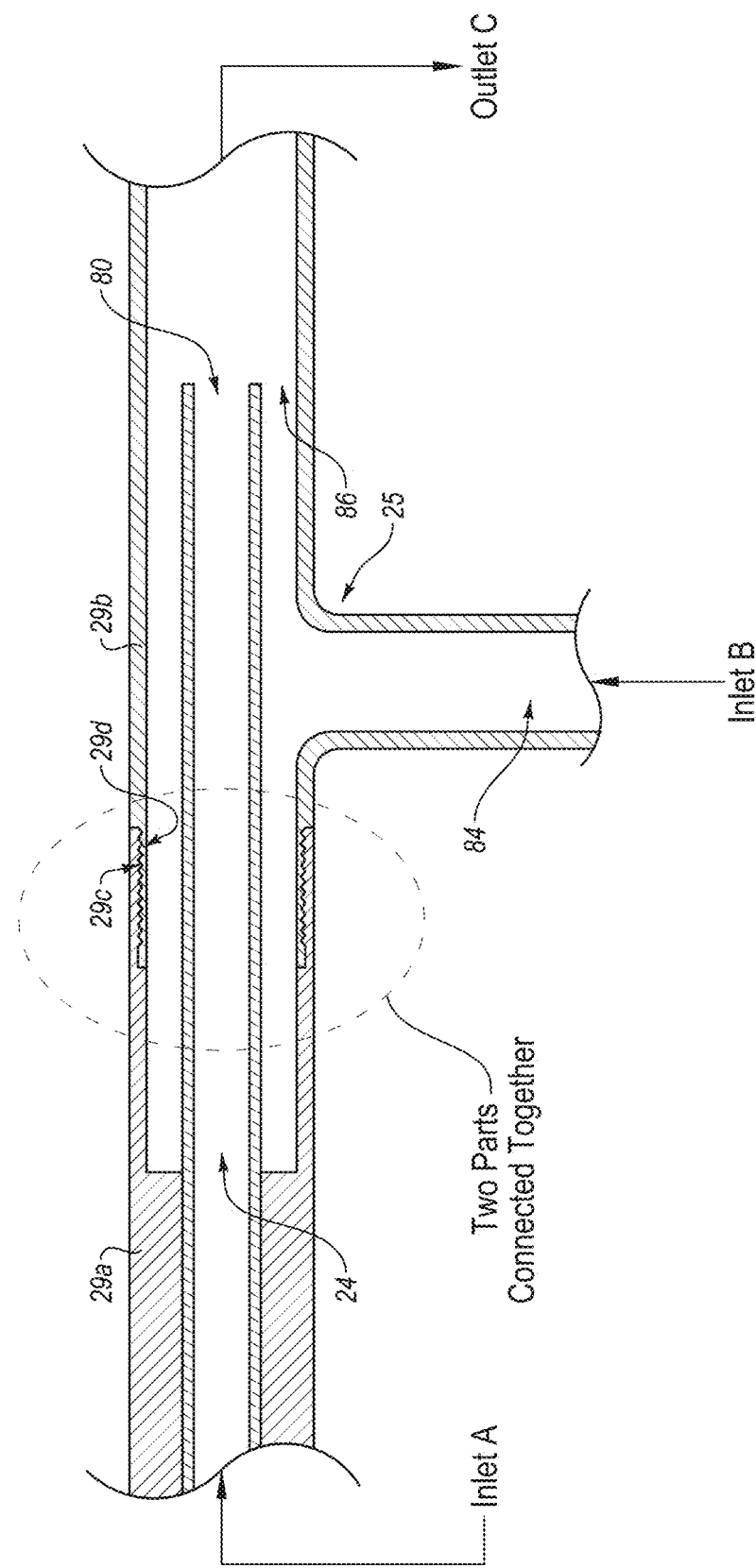
FIG. 3D shows a cross-sectional view of an embodiment of a particle extruding system that extrudes particles into a carrier fluid.

FIG. 3C shows a unitary member that includes the extruder 24 formed into the housing 27 that also includes the extrudate conduit 26 and inlet (Inlet B) from the carrier fluid conduit 84 in order to form the orifice contactor 25. Here, Inlet A can be coupled to the wax conduit 46, Inlet B can be coupled to the carrier fluid inlet 84, and Outlet C can be coupled to the particle collector 28 or to an extrudate conduit that is then coupled to the particle collector 28. FIG. 3D shows an extruder housing 29a separate from an extrudate conduit housing 29b, which are fastened together, such as both the extruder housing 29a and extrudate conduit housing 29b having matching threads 29c, 29d that can be threaded together. However, it should be recognized that the orifice contactor 25 can be prepared in other configurations.

Figure 4A:
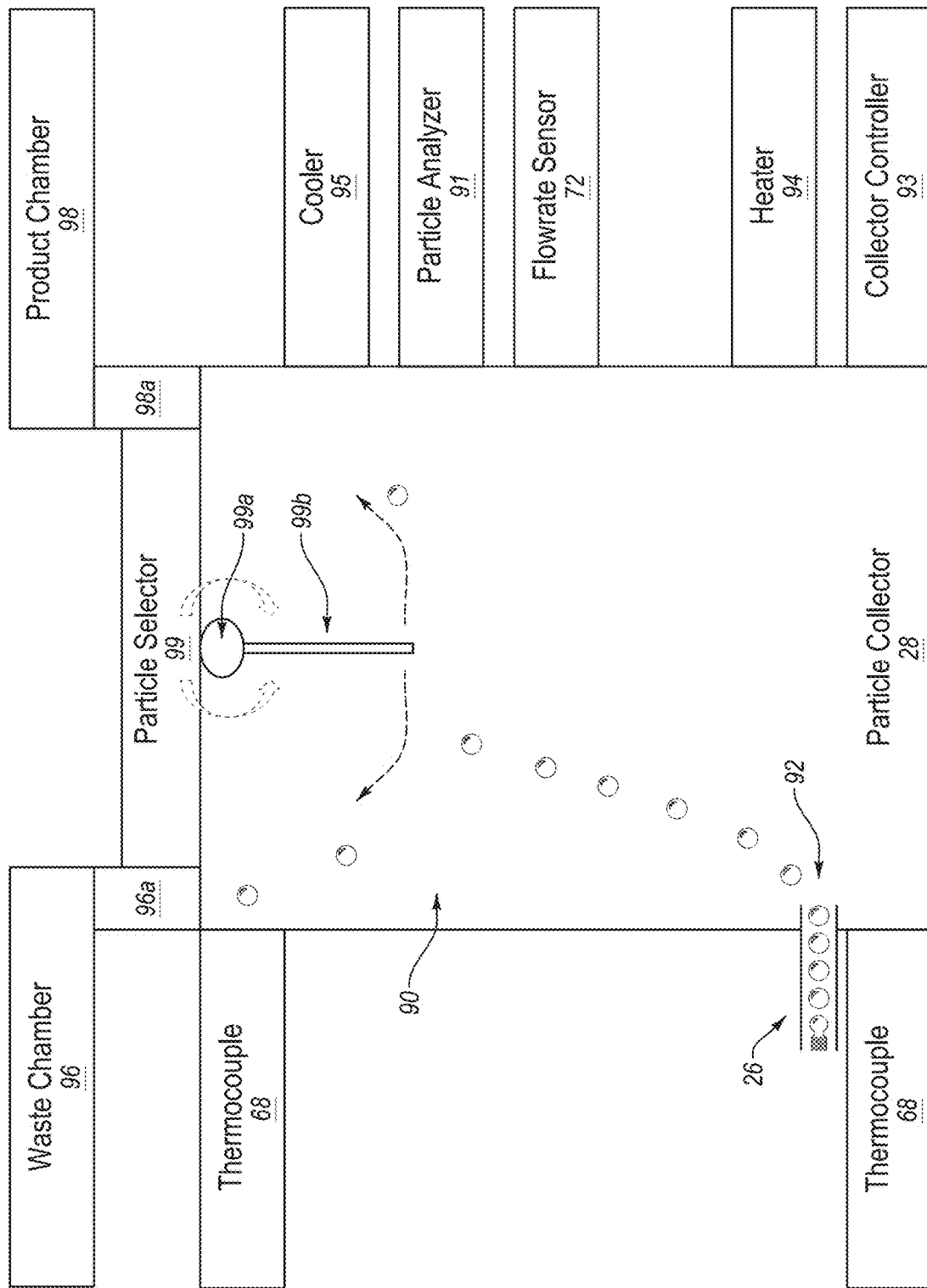
FIG. 4A shows a schematic representation of an embodiment particle collector system.
Figure 4B:
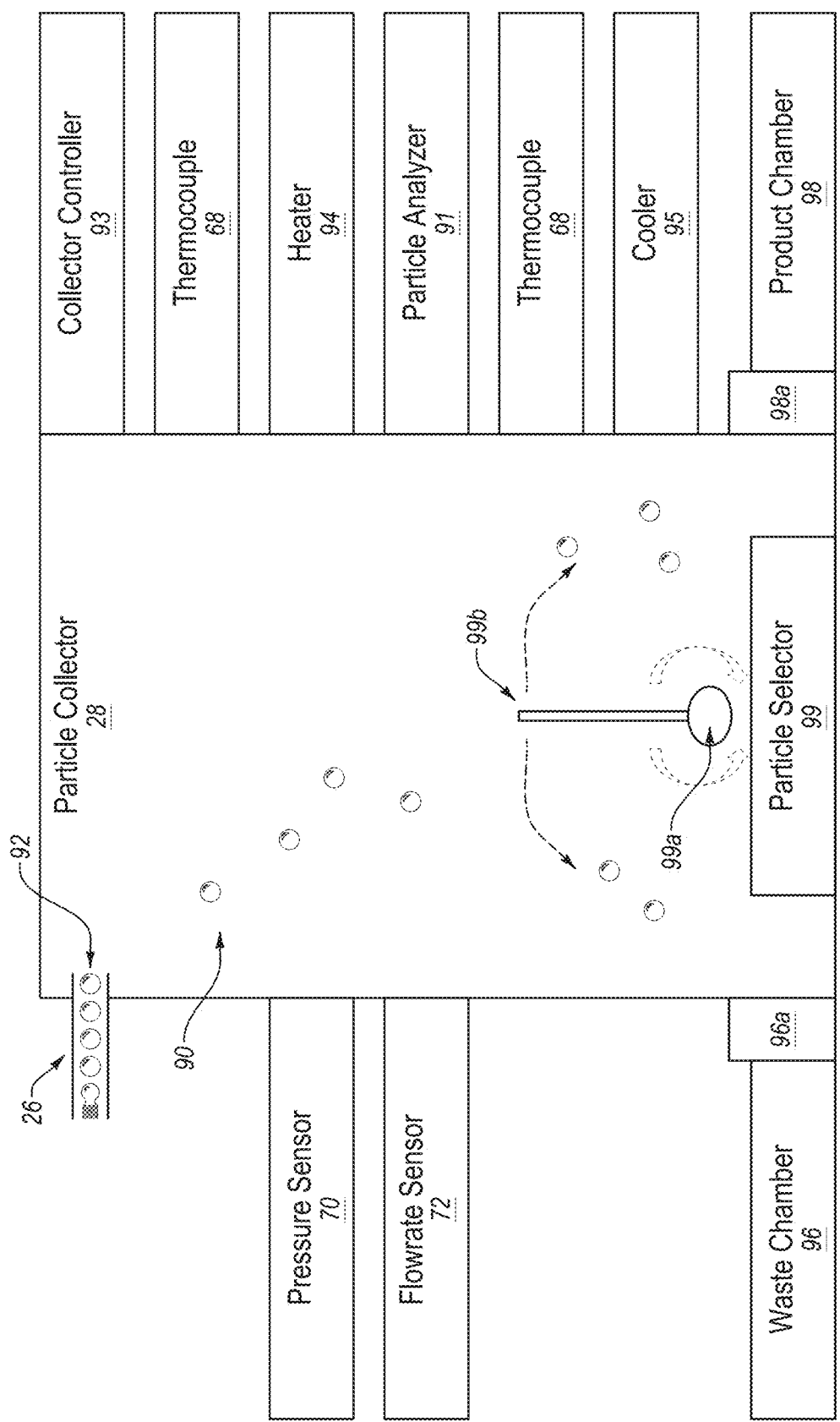
FIG. 4B shows a schematic representation of an embodiment particle collector system.

The particle collector 28 can be present in various configurations. In one example, the particle collector includes a narrow elongate chamber 90 that is vertically oriented; however, the chamber 90 may be any suitable dimension. In one aspect shown in FIG. 4A, the particle collector 28 includes a chamber 90 that is filled with the carrier fluid. The chamber 90 includes a particle inlet 92 that fluidly couples the extrudate conduit 26 to the particle collector 28. A heater 94 is coupled with the particle collector 28 so that the temperature and temperature gradients within the chamber 90 can be controlled as desired or needed to provide heat to increase temperatures. Similarly, a cooler 95 is coupled with the particle collector 28 so that the temperature and temperature gradients within the chamber 90 can be controlled as desired or needed to provide cooling to reduce the temperatures. The heater 94 and cooler 95 can be operated cooperatively so that desired temperature zones and temperature gradient can be created to facilitate particle formation and hardening. A particle selector 99 can be included that selects particles for being provided to the waste chamber 96 via a waste outlet 96a or to a product chamber 98 via a product outlet 98a. The particle selector 99 can have various configurations for selecting particles. In one aspect, the particle selector 99 can include a rotating member 99a (e.g., motor) that rotates a rotatable arm 99b so that rotation in one direction causes the particles to flow to the waste outlet 96a and rotation in the other direction causes the particles to flow to the product outlet 98a. The rotatable arm 99b may extend across the chamber 90 to contact a side surface to form a barrier ramp that directs the particles to either the waste outlet 96a or the product outlet 98a. A particle analyzer 91 can be included that analyzes the particles in order for the particle selector 99 to make the proper selections as to waste or a product. The particle analyzer 91 may use optics to determine the size of the particles for selection or exclusion; however, any other analytical technique may be used or pre-programmed based on machine runtime. As shown in FIG. 4A, the particles are more buoyant than the carrier fluid, such that the carrier fluid is denser than the particles so that they float upward for selection. However, FIG. 4B shows the particles being denser than the carrier fluid so that the particles sink. It should be recognized that the particle collector 28 of FIG. 4B may operate substantially as the particle collector 28 in FIG. 4A with the orientations of particle travel being reversed.

For example, the segments of the wax particles 85 of the carrier fluid 87 that exits the orifice contactor 25 are pumped through the extrudate conduit 26 and then directly into the particle collector 28. The particle collector 28 can include a tall column of carrier fluid in the chamber 90, a heating unit (e.g., heater 94) and cooling unit (e.g., cooler 95), and a particle selector 99 to select particles. The fluid in the chamber 90 feeds into the waste collection chamber 96 or product collection chamber 98 via a rotatable arm 99b. The arm 99b is able to route the solidified particles to either the waste chamber 96 or product chamber 98. The fluid can be the same as the carrier fluid or it could be any fluid that is immiscible with wax. In FIG. 4A, the carrier fluid has a higher density than the wax and a boiling point higher than the melting point of wax. However, in FIG. 4B, the carrier fluid has a lower density than the wax and a boiling point higher than the melting point of the wax. With the aid of the heating and cooling units, a temperature gradient is established across the vertical length of the chamber 90. The point at which the molten wax enters the particle collector 28 can be maintained at the same temperature as the extrudate conduit 26 and carrier fluid flowing therein, and the temperature is gradually decreased along the length of the chamber 90 until the end of the chamber (e.g., top in FIG. 4A, bottom in FIG. 4B) is maintained at a temperature that is below the solidification temperature of the wax. This temperature gradient across the vertical length of the particle collector 28 facilitates the molten wax becoming completely solidified as it flows through the chamber 90 before it flows into the waste collection chamber 96 or product collection chamber 98.

Thermocouples 68 (e.g., one or more) and pressure sensors 70 (e.g., one or more) may be located in any location of the particle collector 28 so that the temperature and pressure of the carrier fluid within the chamber 90 can be monitored. Also, a flowrate sensor 72 may be operatively coupled to the particle collector 28 so that the flowrate of carrier fluid may be monitored. A collector controller 93, which may be part of the control system 32, can be operatively coupled with the heater 94, cooler 95, thermocouple 68, pressure sensor 70, and/or flowrate sensor 72 so that parameters can be measured and analyzed by the collector controller 93 so that operating instructions can be provided so that the carrier fluid is at a desired temperature, temperature gradient, and pressure and flowing through the chamber 90 at a desired flowrate to the waste chamber 96 or product chamber 98.

The wax entering into the chamber 90 can be molten in a fluid state or in a particulate form that is solidifying. While the wax flowing through the extrudate conduit 26 may be particles as shown, it may also be in the form of a column so that there are pulses of wax separated by pulses of carrier fluid.

Although generally it is preferred that the carrier fluid has a higher density than the wax beads, it may not always be feasible, and especially when solid loaded wax beads are produced that include agents in the wax (e.g., organic or inorganic agents, described in more detail here). In this instance, the extrudate conduit is attached to the top of the fluid column (e.g., chamber) of the particle selector as shown in FIG. 4B, and the molten wax beads descend through the fluid, due to gravitational force, and exit into the waste chamber or product chamber, which are connected to the bottom of the fluid column. There is still a temperature gradient maintained across the length of the fluid column, with the top of the column being maintained at molten wax temperature and the bottom maintained at below the melting point of the wax.

In one embodiment, the entire fluid column of the particle collector can be replaced with tubing. The extrudate conduit can be directly connected to a length of tubing that can function as the particle collector. At the other end, the tubing is connected to the pivoting arm of the particle selector. The length of tubing required can be determined by the desired temperature gradient and the time needed for the molten wax to flow through the tube and solidify before entering the waste collection chamber or product collection chamber. In general, a tube length of 20 cm is sufficient in many instances, but can range from 15-25 cm, 10-30 cm, 5-35 cm, or longer lengths. In one embodiment, the tubing length can be maintained and a secondary coolant fluid is pumped into the tubing to co-flow with the wax and carrier fluid to actively solidify the wax particles. Such a secondary coolant fluid can be introduced at any point from the carrier fluid reservoir 60, carrier fluid conduit 66, or in the extrudate conduit 26, or in the particle collector 28. For example, FIGS. 4A and 4B show the particle collector 28 in a schematic representation, and it should be recognized that the elongate chamber 90 can be configured as a tube. In another example, the tubular elongate chamber 90 may have dimensions similar to the conduit 86 or extrudate conduit 26, or larger.

Additionally, the system can be programmed such that from initiation of the particle forming process to a specific defined runtime (e.g., pre-programmed run-time) all of the formed particles are sent to the waste chamber. Then, after the defined run-time, the particle selector can then send the subsequently formed particles to the product chamber. The defined runtime can be set to be the lead time until steady-state operation is achieved, which can vary between systems and desired particles. For example, the defined runtime where particles are automatically discarded as waste can be 30 seconds, 1 minute, 2 minutes, 3 minutes, 5 minutes, or 10 minutes. In one aspect, one or more test runs can be performed to determine the lead time until steady state, and that lead time can be used to define the runtime where particles are discarded as waste. After the runtime where the particles are sent to waste, the system can operate as described herein with the particle selector selecting inadequate particles for waste and selecting suitable particles for products. As such, a switch from waste to product instruction can be programmed into the system so that the system can automatically execute the switch at a defined time.

The system may also be programmed such that after a defined steady state period, or defined time of particle product collection, the system can switch so that all subsequent particles are sent to waste. As such, a switch from product to waste instruction can be programmed into the system so that the system can automatically execute the switch at the defined time.

Also, as the control system monitors the different components, thermocouples, sensors, and overall operation, deviations from optimal or normal operations can be identified. Once such a deviation is identified, the system can cause the particle selector to switch from product to waste so that the particles that are formed during the deviation are not collected as products. For example, changes in the operational conditions of the pumps, heaters, coolers, changes in temperature, and/or changes in flow rates or pressures may indicate that subsequent particles may be deficient so that they can be sent to waste and not collected as products. Also, the level of wax in the wax reservoir or level of carrier fluid in the carrier fluid reservoir may be monitored and such level(s) are below a defined threshold, the system can switch the particle selector to send subsequent particles to waste.

In one embodiment, the system can be programmed with the lead time until reaching steady state where all particles are sent to waste, the production time during which particles are analyzed for being waste or products (or all particles sent collected as products), and a shutdown time after the steady state where the system is initiating and performing a shutdown operation. As such, only the particles produced during the steady state operation time can be collected as products, otherwise, during the lead time and during shutdown time the particles are automatically sent to waste. Accordingly, the determination to send all particles to waste may be tied to the operation of a component, such as wax pump or carrier pump, wax heater, carrier heater, or other, where the shutdown of such a component can trigger the particle selector to send all subsequent particles to waste. When the system is automated, the timing of such shutdown of one or more components is programmed, and such programming may also include programming the particle selector to automatically send particles to waste before or when a component starts the shutdown process. For example, at a defined time prior to the wax pump shutting down, the particle selector can switch so that the subsequently formed particles all go to waste, such as 30 seconds, 1 minute, 2 minutes, or other time before the programmed shutdown time.

Figure 5A:
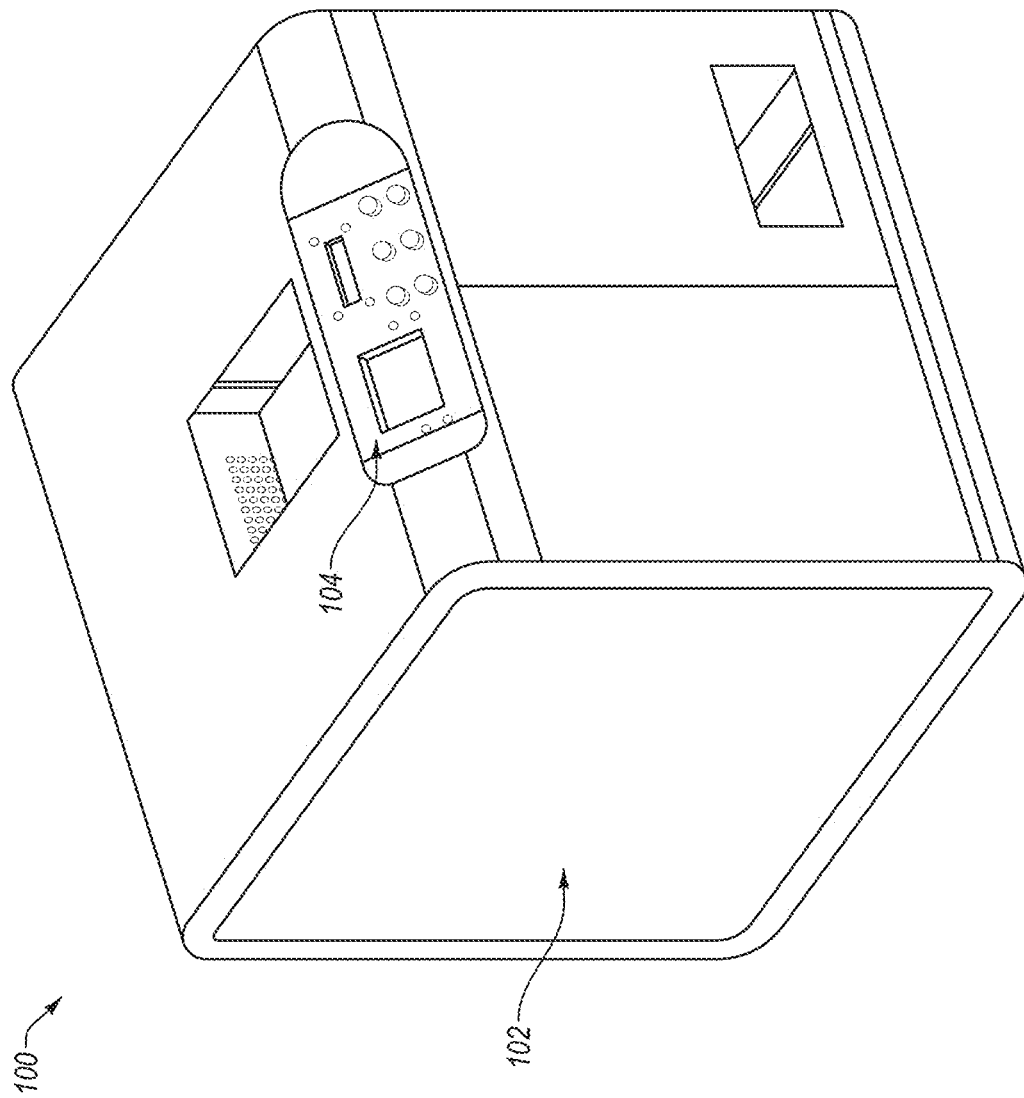
FIG. 5A shows an embodiment of a housing that contains a particle forming system.

In one embodiment, as shown in FIG. 5A, the system described herein and illustrated in the figures can be configured as a unitary device 100. The unitary device 100 includes a housing 102 that contains the components therein (e.g., as shown in FIGS. 2A, 2B, 2C, 3A, 3B, 3C, 3D, 4A, 4B, and others). The housing 102 can include a user interface 104 that includes input means (e.g., touch screen, knobs, buttons, dials, etc.) and display means (e.g., screen), which can be used for operation. While not specifically shown, the housing 102 can include ports for receiving the wax to be formed into wax particles, the carrier fluid, and for obtaining the wax particles therefrom. The wax particle formation protocol can utilize precise temperature control and maintenance throughout its operation, which can include heating and optionally selective cooling. Heating performed by the heating system and individual heaters can be achieved via an IR heater, heating pads, water bath, heat exchanger, or other means of heating. For example, the solid wax is supplied into the wax reservoir with continuous heating to melt the solid wax as fast as possible into molten wax and to maintain it above the wax melting point, such as at least 4° C. above the wax melting point. The heating can be extended to the carrier fluid and the orifice contactor as well as the conduits and particle collector. The components may be kept at a constant uniform temperature that keeps the wax molten until reaching the extrudate conduit and/or particle collector.

In one aspect, heat is also supplied to the collection unit; however, a temperature gradient is maintained either naturally with ambient conditions or with an active cooling system. Active cooling can be performed with any cooling technology, including refrigeration, temperature conditioning, heat exchange, cold water baths, or other. In one aspect, the carrier fluid within the extrudate conduit or particle collector is heated to a temperature or maintained at the temperature above the melting point of the wax. At the end of the particle collector (~10% of the height from the outlets), the temperature can be maintained at least 2-3° C. below the solidification temperature (e.g., below the melting point) of the wax. The heating and cooling can create a selective temperature gradient for particle solidification. In one example, circulating cold water at the region near the outlets of the particle collector can also cool the outlets and form the temperature gradient.

Figure 5B:
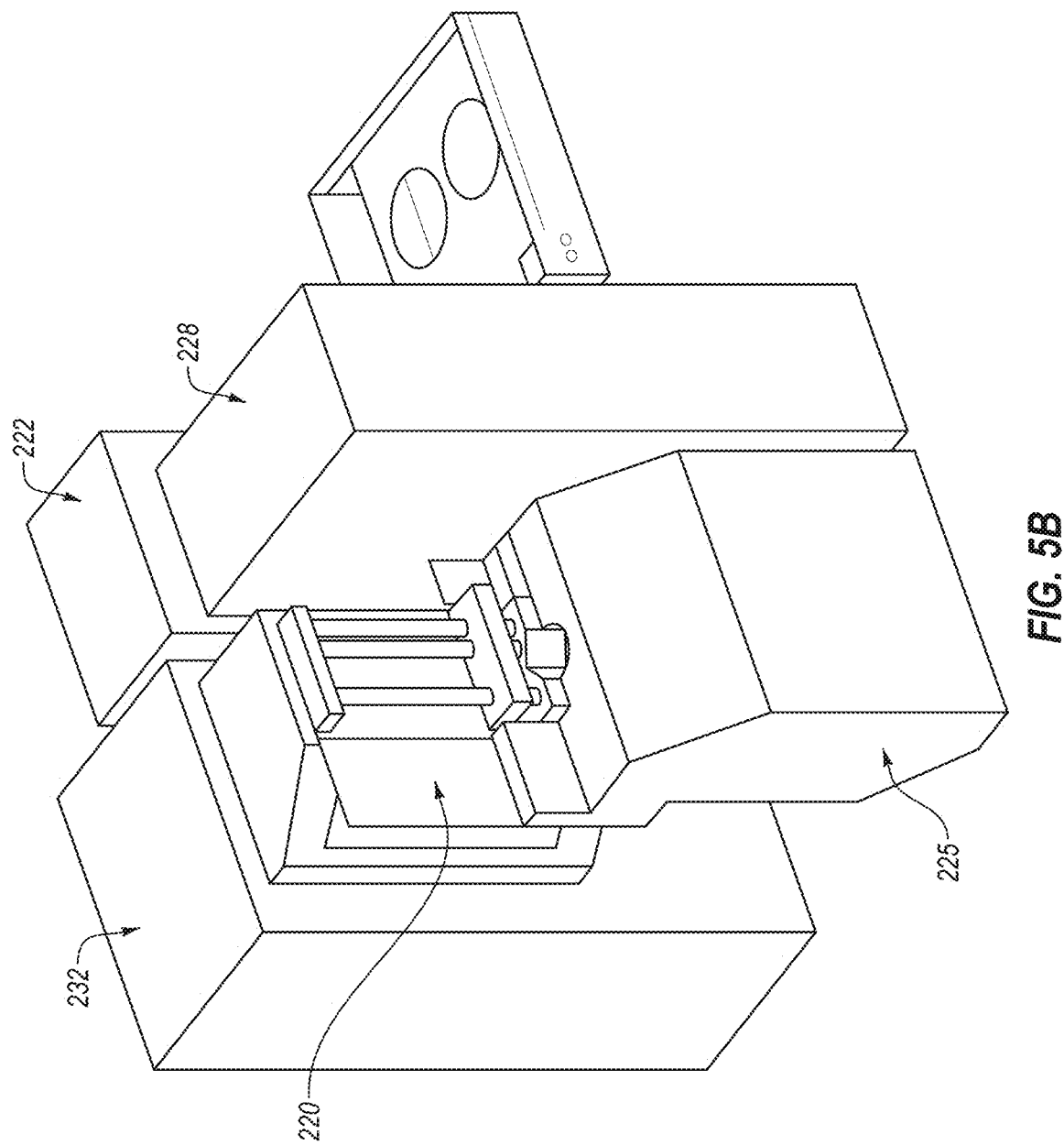
FIG. 5B shows an embodiment of components of a particle forming system contained in the housing of FIG. 5A.

FIG. 5B shows the carrier fluid unit 222, collection and heating unit 228, wax dispensing unit 220, orifice contactors and heating unit 225, and control system unit 232. The components of FIG. 5B can be retained within the housing 102 of FIG. 5A.

Figure 6:
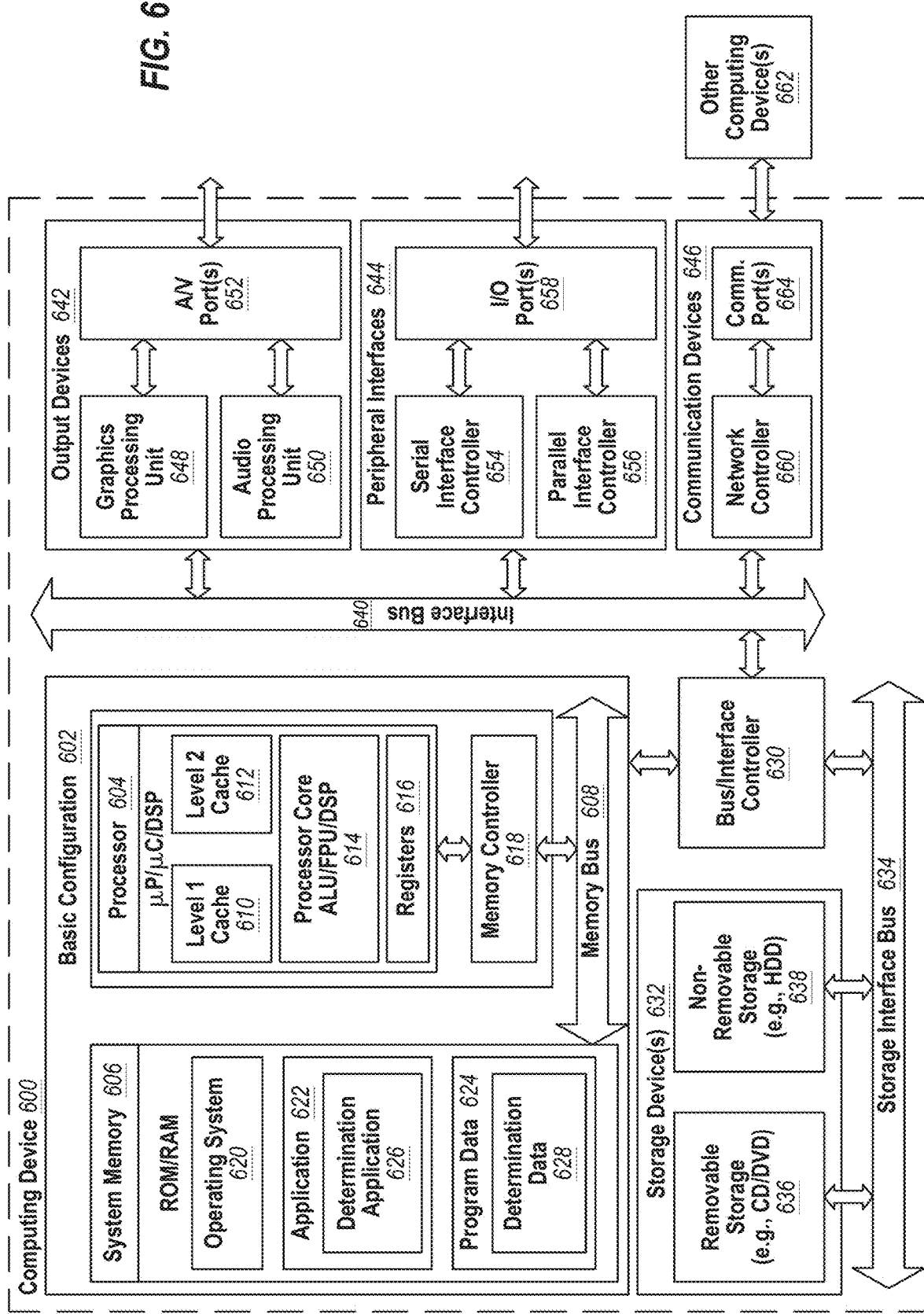
FIG. 6 shows a schematic representation of a computing system that can be used as a controller for a particle forming system.
Figure 6A:
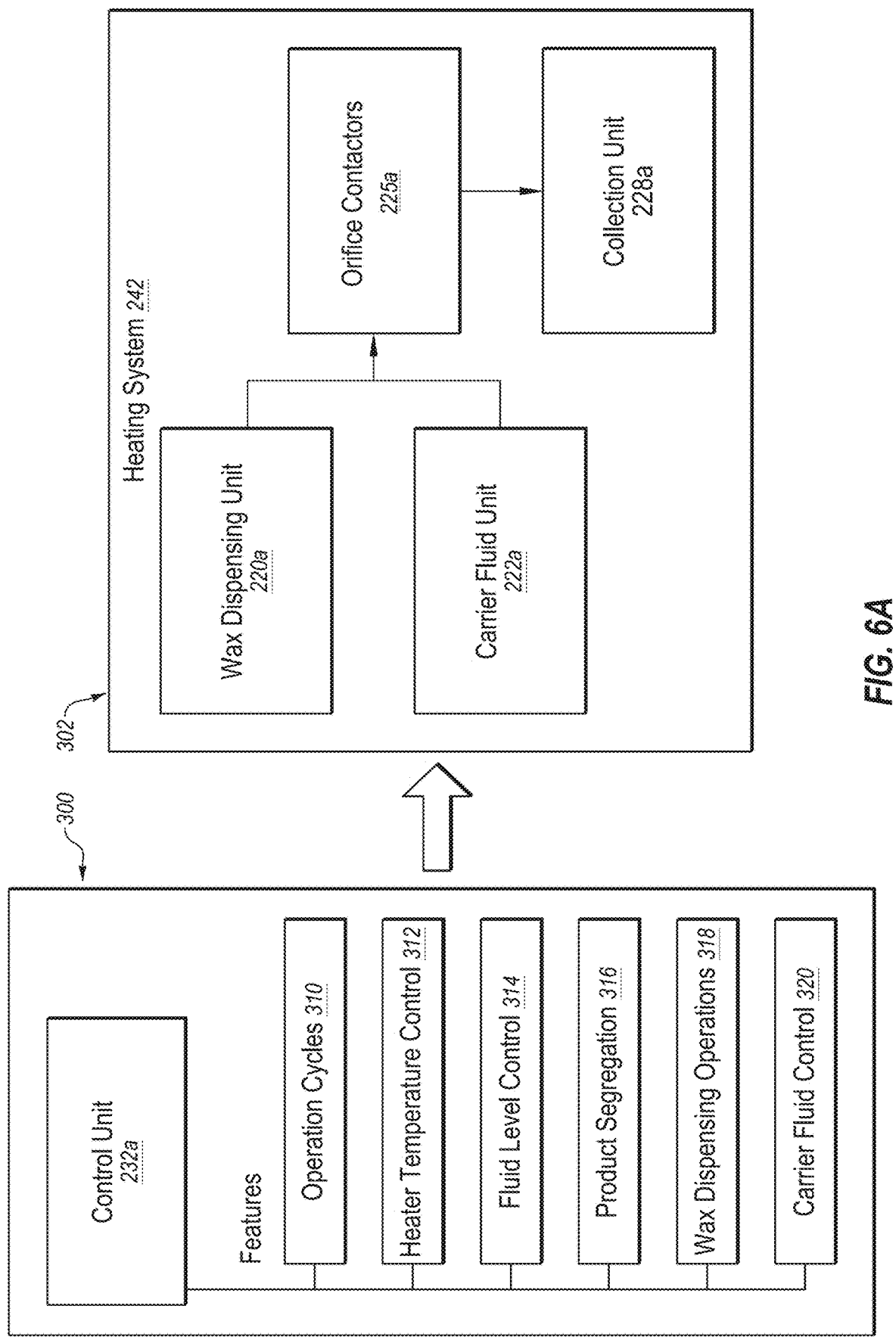
FIG. 6A shows a schematic representation of a control environment of a particle forming system.

The wax particle forming system described herein includes the control system (e.g., computer functioning as control unit(s)) that allow for automation. FIGS. 6 and 6A illustrate embodiments of the control system. FIG. 6 shows a computer (e.g., computing device 600) that can be used for any controller or control unit or control system described herein. As such, the production of wax particles can be fully automated and operated through the control system 300, for example as shown in FIG. 6A. The control system 300 can obtain data from temperature sensors (e.g., thermocouples), pressure sensors, flowrate sensors, the various controllers for the different components, linear motors (e.g., pumps having linear motors, such as in syringe pumps), and detectors (e.g., particle analyzer) that control the production of wax particles (e.g., wax beads), any of which that are described herein and/or illustrated in the figures. Upon switching on the wax particle forming system 302, the heating system 242 (e.g., including the individual heaters) is activated, where the particle collector of the collection unit 228a is also heated. Once the desired temperature gradient in the particle collector is achieved and the wax and carrier fluid have reached their pre-set temperature(s), the carrier fluid is pumped through the carrier fluid conduit of the carrier fluid unit 222a and through the extrudate conduit of the orifice contactors 225a. After a pre-determined time or after reaching a steady state condition with carrier fluid flow rates, the wax is then pumped to flow through the wax conduit to the extruder of the wax dispensing unit 220a so as to be extruded into the carrier fluid within the extrudate conduit, or generally in the orifice contactor. The wax is flowed through the extrudate conduit with the carrier fluid to the particle collector, where wax particles are produced. In one aspect, the wax particles that are produced in the first few minutes of operation or when tagged by the particle analyzer are channeled into the waste collection chamber to account for the initial variability that may be present or inherent in the system start-up dynamics or until steady state conditions are achieved. The wax particles in the particle collector are monitored via the particle analyzer (e.g., camera with a live feed), which allows selection of defective wax particles (e.g., too small, too large, misshapen, etc.), and selection of suitable wax particles for products. When the steady state of wax particle production is achieved with uniform wax particles, the control system can activate the particle selector for collection of the wax particles into the product chamber.

The control unit 232a can implement various control instructions, such as operation cycles 310, heater temperature control 312, fluid level control 314, product segregation 316, wax dispensing operations 318, and carrier fluid control 320, among other control instructions such as described herein.

The wax particle forming system can be operated at a steady state until a shutdown protocol is implemented. The wax particle forming system can include a protocol that is performed for shutdown and controlled by the control system. The shutdown protocol can follow a distinct series of steps when shutting down the system so that it is ready to be initialized for future operations. First, the heating of the wax reservoir is terminated by shutting down the wax heaters and the flow of wax into the extruder of the orifice contactor is stopped by shutting down the wax pumps. Meanwhile, the heated carrier fluid is continued to be pumped through the carrier fluid conduits, extrudate conduit, and optionally the particle collector to clear any residual wax in the orifice contactor, conduits, or particle collector. After a defined time or after the wax is cleared, the heating for the carrier fluid in the reservoir is then turned off. The carrier fluid pumps are also turned off before, during or after the heating of the carrier fluid is terminated. Once the temperature of the system returns to a pre-set temperature, the system can be switched off.

In one embodiment, the carrier fluid in the carrier fluid reservoir may be different from the fluid in the particle collector at the beginning of a run to produce wax particles. As the particles are produced and the carrier fluid enters into the particle collector, the carrier fluid will increase in percentage until substantially all of the fluid in the particle collector is carrier fluid from the carrier fluid reservoir. However, if there are significantly different densities of the different fluids, then the carrier fluid may be drawn off from the particle collector to allow two different fluids therein with a gradient there between, where the denser fluid would accumulate lower in the particle collector. However, the carrier fluid and particle collector fluid may be the same.

Figure 7A:
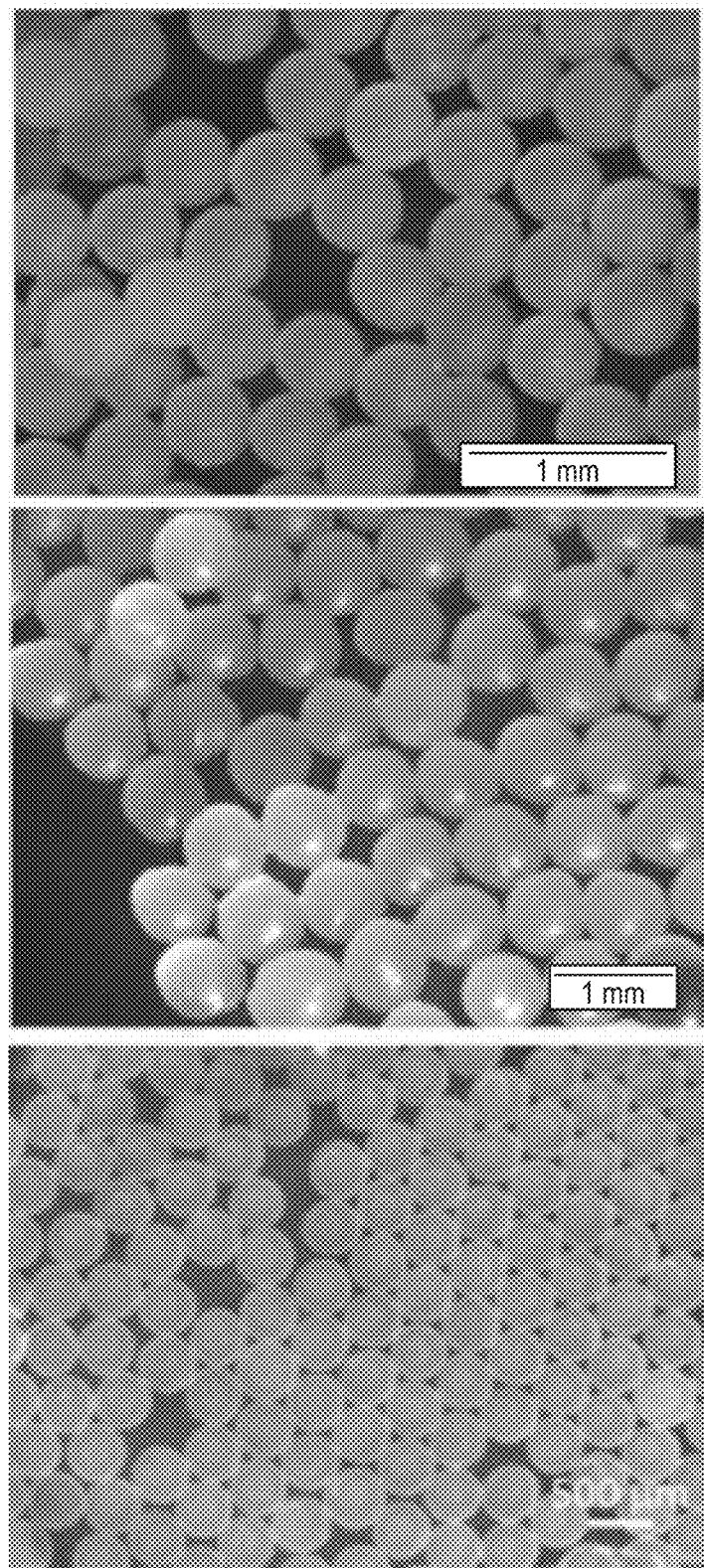
FIG. 7A shows images of particles formed with an embodiment of a particle forming system.
Figure 7B:
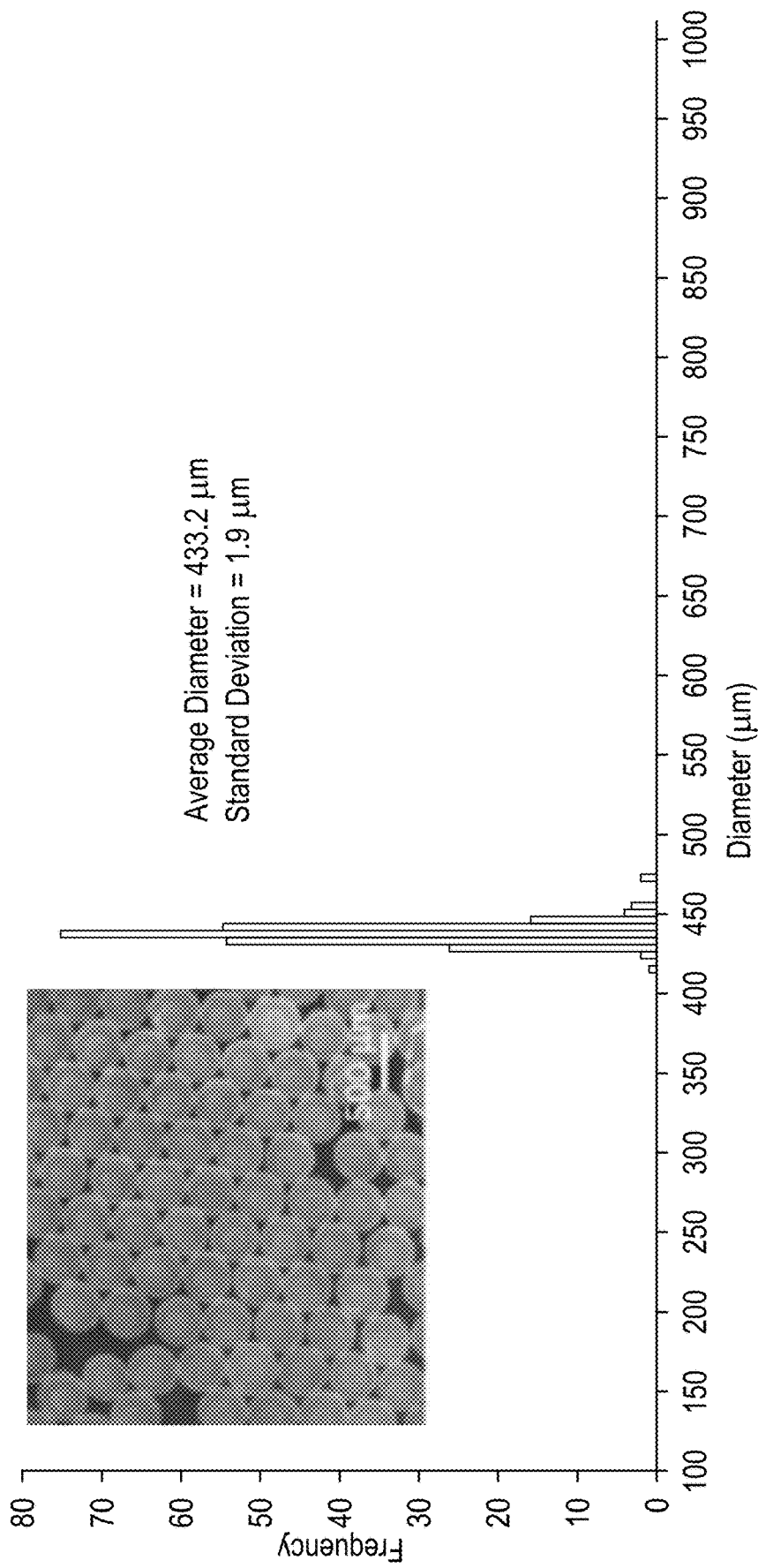
FIG. 7B is an image of particles formed with an embodiment of a particle forming system and a graph of particle diameter distribution.
Figure 7C:
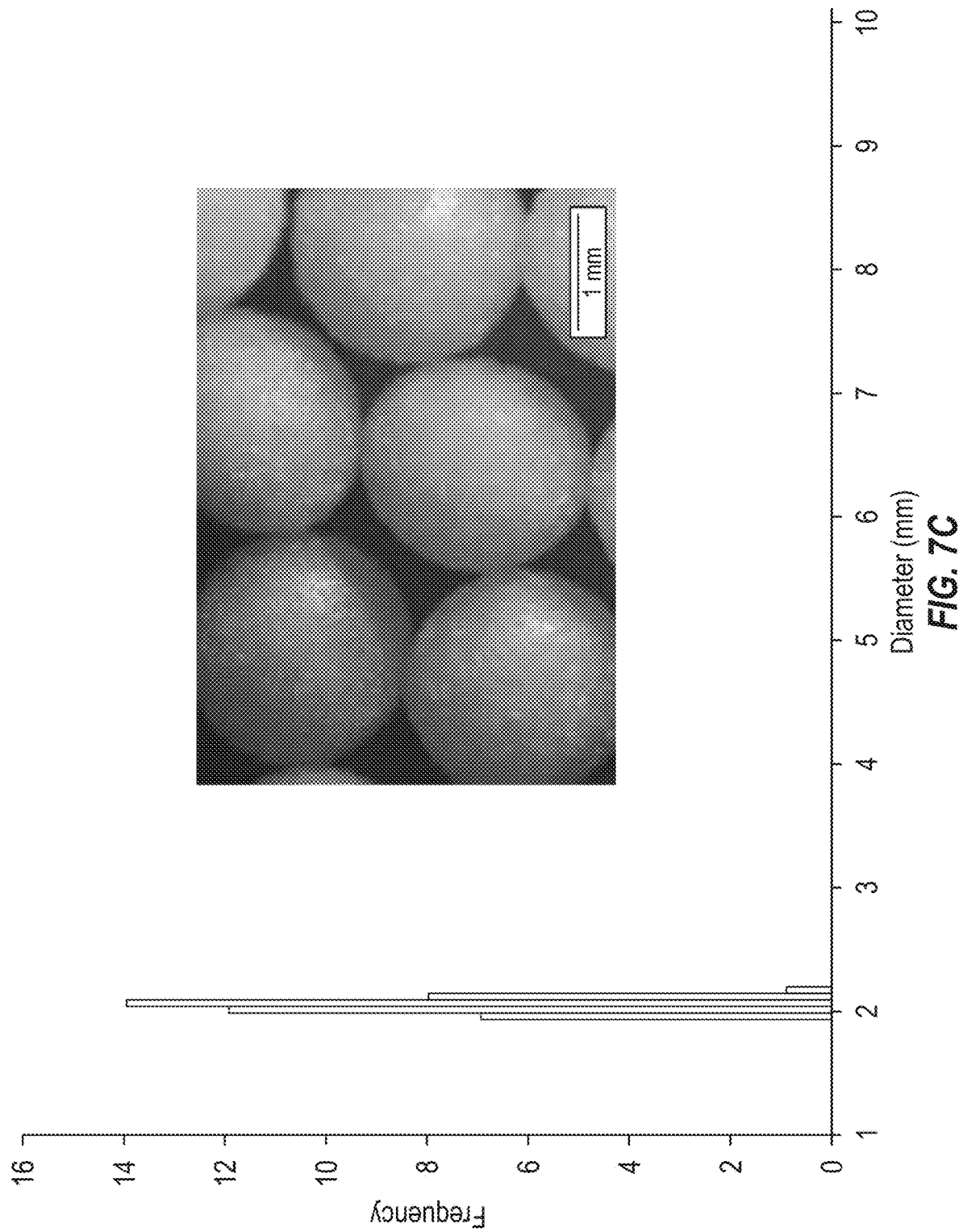
FIG. 7C shows an image of particles formed with an embodiment of a particle forming system and a graph of particle diameter distribution.

The system can be operated to form wax particles of various size, which are presented as beads having a uniform size from a single operational run. FIG. 7A shows examples of wax beads that are formed, which range in sizes. FIGS. 7B (average diameter=433.2 microns with standard deviation of 1.9 microns) and 7C (particles centered around 2 mm) show the narrow range of particle sizes, which can be considered to be monodisperse, that are achieved with the system.

Figure 11:
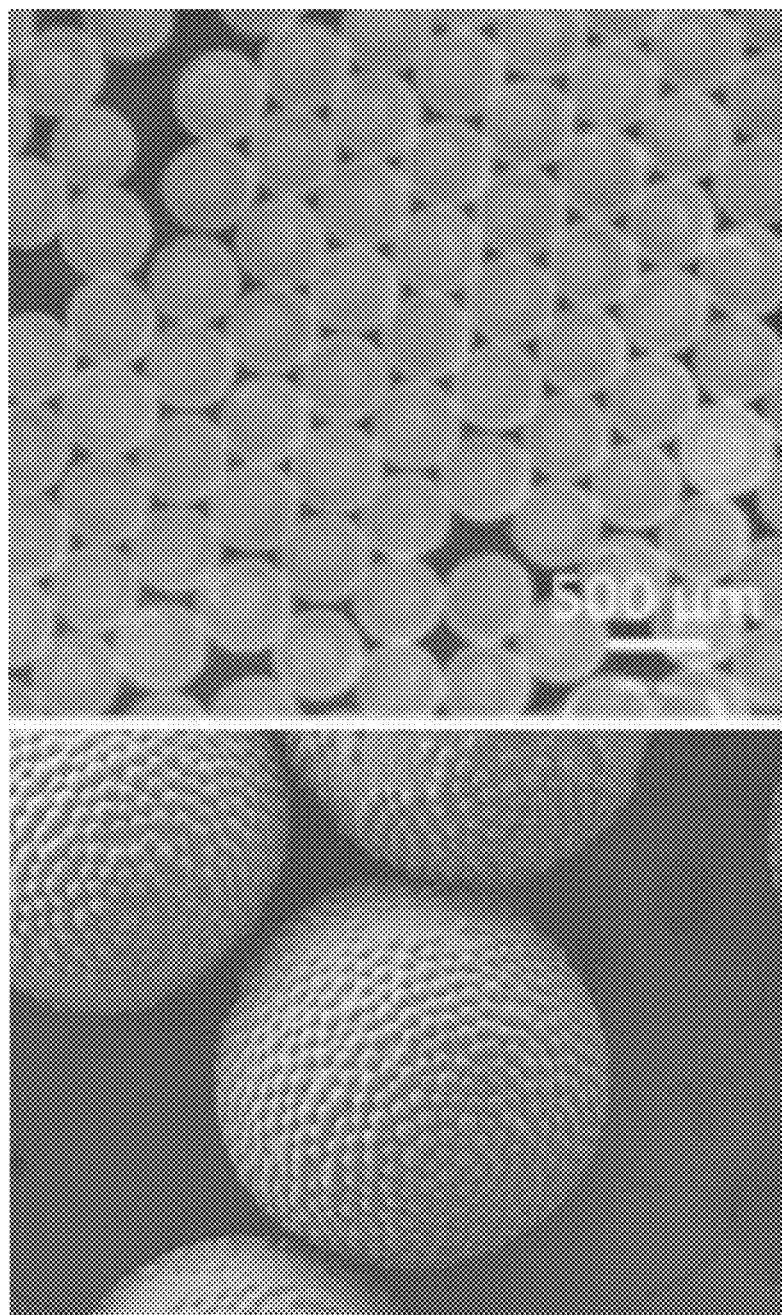
FIG. 11 includes images of micronized solids-loaded beeswax.

In one embodiment, the wax particles can be formed to include various agents. The agents can range from pharmaceuticals, cosmetics pesticides, fungicides, antimicrobials, chemicals, fillers, or other materials, which may be micronized solids. Often, the agent is a micron-sized solid particle of various chemical substances. As such, the wax reservoir can optionally be configured as a mixer to mix the agent with the wax; however the wax reservoir may not be configured as a mixer for inclusion of agents in the wax particles. The operation of the system can form micronized solids or other agents loaded into the wax particles (e.g., wax beads). For producing micronized solids or other agents loaded in wax particles, the operation of the system is similar to the protocols described herein, with the modification of the agent being introduced into the wax reservoir. In one example, micronized solids or other agents are blended together with wax (e.g., which can be molten wax or solid wax blending) prior to being loaded into the wax reservoir. In this instance, molten wax containing micronized solids is loaded into the wax reservoir, which can be in the form of a syringe pump. The micronized solids or other agents can be crystalline or amorphous and may be soluble or insoluble in the wax. In one example, the solids are typically sized at 50 microns or smaller. The volume fraction of solids in the wax can range between about 5-70% by weight, 10-60% by weight, 20-50% by weight, 30-40% by weight, or about 35% by weight. See FIG. 11.

When the wax reservoir is configured as a mixer, or when the carrier fluid reservoir is configured as a mixer, any mixing arrangement or configuration or mixer type may be used. Mixers are common components and reservoirs that are mixing reservoirs can be adapted for the uses herein. Also, any of the conduits or components may include a mixer from the reservoirs up to the extrudate conduit, where the extrudate conduit and particle collector can be devoid of mixers. While mixers are not specifically shown, it should be recognized that the reservoirs, conduits and extruder may include a mixer. Any type of mixer can be used, which can include rotational mixers, auger mixers, static mixers, vibratory mixers, ultrasonic mixers, magnetic stirrers, or other mixers. The type of mixer may be selected for different components that can include mixers. In an example, the reservoirs can include ultrasonic mixers or magnetic stirrers. In another example, the conduits can include static mixers, such as before the orifice contactor (e.g., before the extruder).

In one example, organic materials can be the agents blended with the wax to form wax beads that include organic materials. The organic materials can be blended with the molten wax as described herein before formation of the wax particles. Accordingly, wax beads containing organic materials, such as essential oils, can also be produced with the system described herein. The desired organic material is blended together with molten wax prior to be being loaded into the dispenser. Any organic material that is miscible or soluble in wax can be used. Some examples are essential oils (e.g., Tea Tree oil) and fragrances, as well as extracts of plants, nutraceuticals, dietary supplements, vitamins, pharmaceuticals, cosmetics or other organic materials. Typically, organic materials will be soluble in the wax material. In one example, the wax can be edible and the organic material can be a dietary supplement.

In one example, inorganic materials can be the agents blended with the wax to form wax beads that include inorganic materials. The inorganic materials can be blended with the molten wax as described herein before formation of the wax particles. Accordingly, wax beads containing inorganic materials can also be produced with the system described herein. The desired inorganic material is blended together with molten wax prior to being loaded into the dispenser. Any inorganic material that can be blended or suspended in wax can be used. Some examples of inorganic materials are glasses, ceramics, metals, composites, rocks, minerals, catalysts, or others. The wax containing the inorganic materials may be used for providing the inorganic material to an industrial process where the wax can be melted away so that the inorganic material is available for use.

In one embodiment, the orifice contactor can be configured to produce wax particles that have a core and shell configuration. In one aspect, the shell is wax and the core is a liquid. In one aspect, the shell is wax and the core is a different solid. The system can be modified to include an additional reservoir and conduit that provides the core material to the wax in the orifice contactor. Solid materials can be used for the core; however, the material may need to have a melting point lower than the melting point of the wax, and thereby the wax particle is prepared with a liquid core that may solidify into a solid core. The material that forms the core can be immiscible with the wax shell. As such, the example will be provided while discussing a liquid core, where the liquid core can solidify or stay a liquid.

Figure 8A:
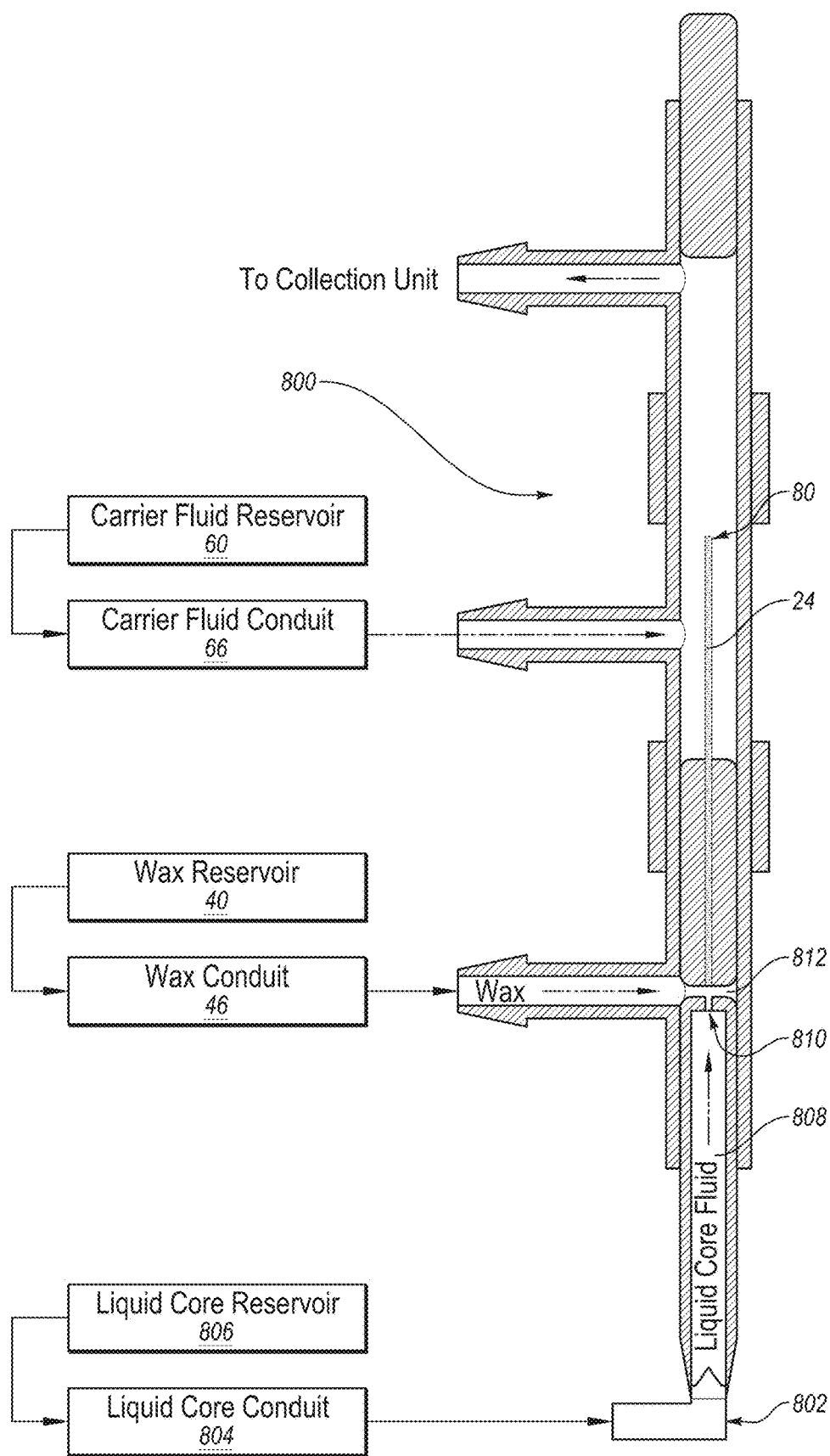
FIG. 8A shows a cross-sectional view of an embodiment of a particle extruding system that extrudes core and shell particles into a carrier fluid.

FIG. 8A shows an example of a multi-stage orifice contactor 800. The multi-stage orifice contactor 800 includes a liquid core inlet 802 that is coupled to a liquid core conduit 804 that receives the liquid from a liquid core reservoir 806. The liquid core material flows through the inlet 802 through a central conduit 808 through a nozzle 810 to the junction point 812 where the wax from the wax reservoir 40 via the wax conduit 46 surrounds the liquid core material. From the junction point 812, the wax containing the liquid core material flows through the extruder 24 and out of the extruder orifice 80 where the carrier fluid (e.g., from carrier fluid reservoir 60 via carrier fluid conduit 66) surrounds the wax so that the liquid core material and wax are co-extruded into the carrier fluid. That is the wax is extruded around the liquid core material such that the carrier fluid is around the wax. The system can be modified to incorporate the multi-stage orifice contactor 800. Thus the multi-stage orifice contactor 800 is similar in design to the orifice contactor that uses only wax and carrier fluid. This arrangement would allow the formation of a wax bead having a liquid/aqueous core that is immiscible with wax. The multi-stage orifice contactor 800 is configured to allow the flow of three streams of fluid to come into contact.

Figure 8B:
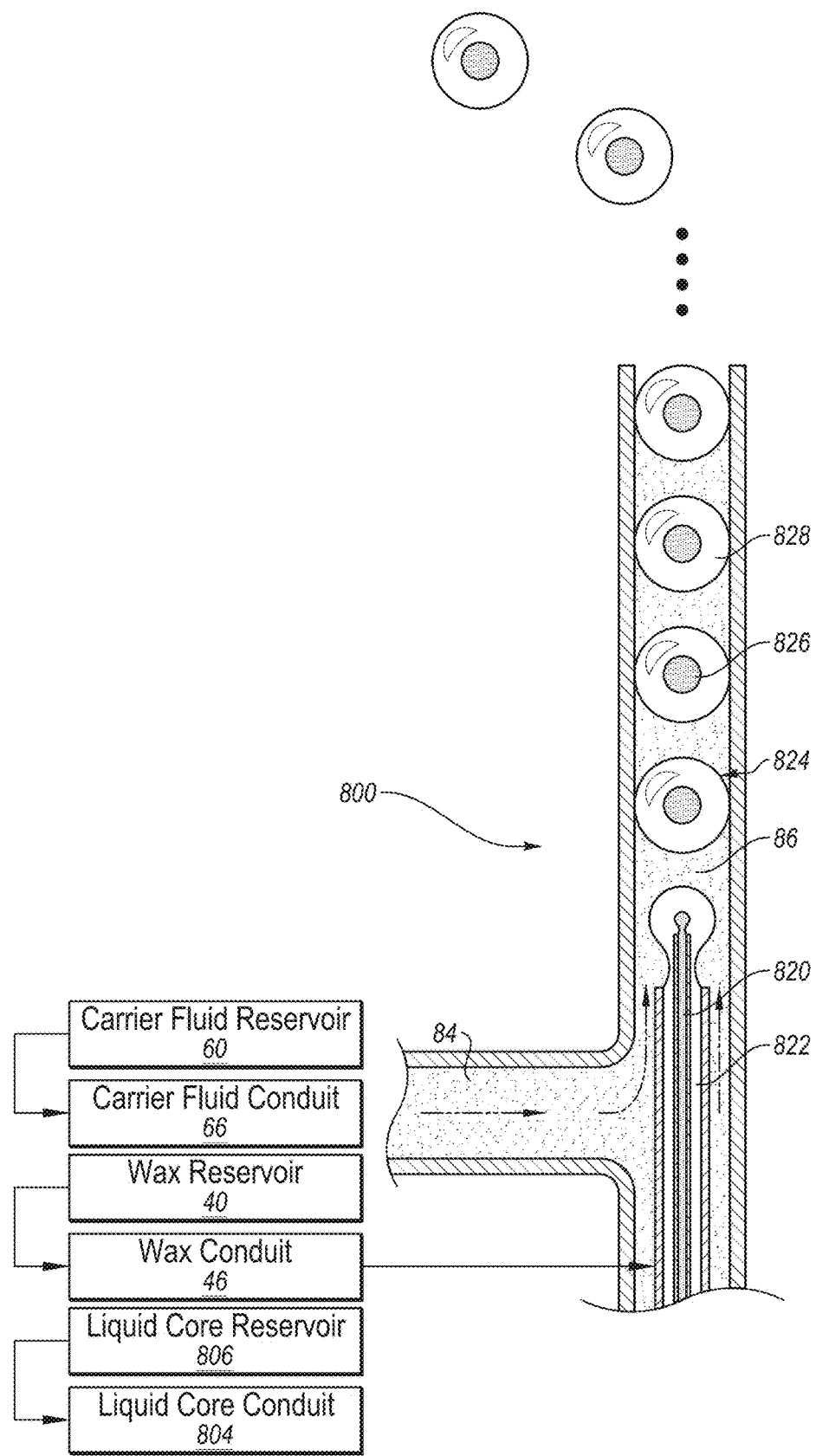
FIG. 8B shows a cross-sectional view of an embodiment of a particle extruding system that extrudes core and shell particles into a carrier fluid.

FIG. 8B shows a configuration where the liquid core conduit 804 passes through the center of the wax conduit 46 so that the wax is extruded around the liquid core material, where both are extruded within the carrier fluid as described herein. The liquid core stream is injected through the wax stream, which in turn flows through the carrier fluid stream. This again leads to a serial alternation of wax with liquid core segments and carrier fluid segments. FIG. 8B shows an internal extruder 820 that extrudes the liquid core material, which is within the wax extruder 822 that extrudes the wax around the liquid core material. The internal extruder 820 within the wax extruder 822 are both within the fluid conduit 86. This arrangement produces core and shell particles 824 having the core 826 and shell 828.

Additionally, it should be recognized that the configuration of the orifice contactor can be changed and modulated as needed or as desired. The modulation of the diameter of the extruder compared to the diameter of the lumen of the extrudate conduit can be modulated in order to change the diameter of the wax particles that are formed. While the extruder and extrudate conduit are described as being generally circular in cross-sectional profiles, the shapes of the cross-sectional profiles of the extruder and/or extrudate conduit may be similarly modulated, such as square, rectangular, oval, triangle, or other shape. As such, the shapes and geometries can be modulated to give rise to products with tunable shapes and sizes. The conduit can also be formed from two or more components that result in the conduit of desired shape.

Figure 10:
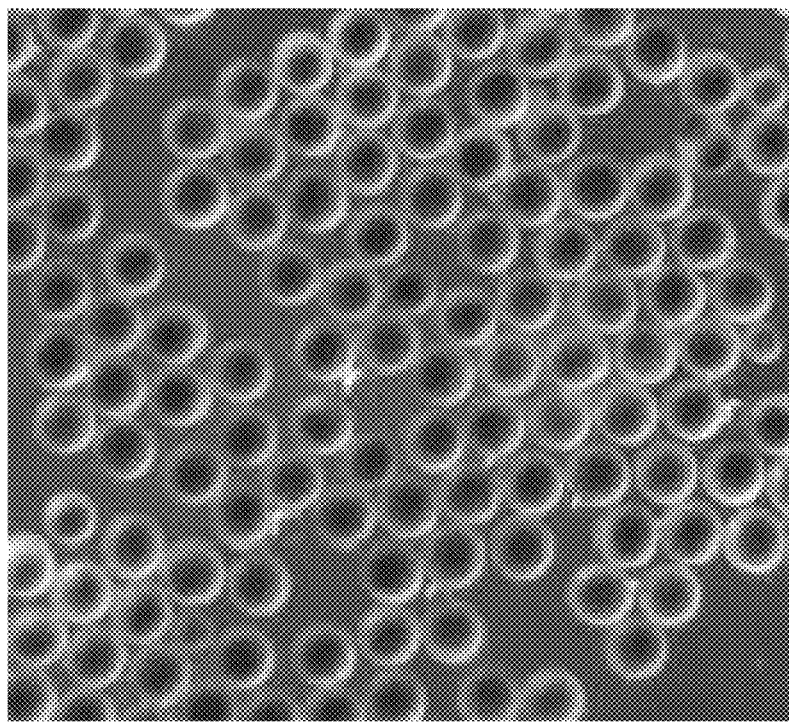
FIG. 10 is an image of shell and core particles.

FIG. 10 shows an example of microparticles with a wax shell and liquid core.

Example 1

Monodispersed beeswax particles can be formed with the system. In order to make monodispersed beeswax particles, water is selected as both the carrier fluid and the fluid in the particle collector. Beeswax has a melting temperature in the range of about 62-65° C. and thus water, a denser immiscible fluid having a boiling point of 100° C., is a suitable carrier fluid and particle collector fluid. Solid beeswax is loaded into the wax reservoir, and water is loaded into the carrier fluid reservoir and particle collector. The control system is operated so that the temperature of the wax reservoir, carrier reservoir, orifice contactor and various conduits is set at about 70° C. The entrance temperature of the particle collector near the extrudate conduit inlet is also set at 70° C., while the outlet temperature at the end opposite of the extrudate conduit inlet (e.g., near waste collector or product collector) is set at 60° C. Once the temperature profiles are programmed, the heating elements are switched on via the control system. Once the beeswax, water and orifice contactor have reached the set temperature, the control system turns on the cooling unit at the end of the particle collector opposite of the extrudate conduit inlet (e.g., near waste collector or product collector). When the temperature gradient across the fluid in the particle collector is achieved, the control system turns on the carrier fluid pump (e.g., at the carrier fluid reservoir). Water is then circulated through the orifice contactors and into the particle collector. The flowrate of water can range from 0.5-10 ml/min, depending on the size of the wax bead to be generated. Once water flows through the orifice contactor and into the particle collector, the wax pump (e.g., at the wax reservoir) is switched on and molten beeswax is pumped through the orifice contactor at a much slower rate than the water carrier fluid. The typical flowrate for wax is 0.025-0.1 ml/min. The flowrate of wax is typically at least 10 times (e.g., 10×) lower than the carrier fluid. For instance, to make 0.5 mm beeswax beads, the wax flow rate is set at 0.1 ml/min and carrier fluid is set at 5 ml/min. For beeswax beads the size of 0.3 mm, the wax flow rate is set at 0.025 ml/min and water is 0.75 ml/min. Accordingly, smaller particles can be achieved with smaller flowrates. In both instances, the orifice contactor remains the same with the extruder orifice having a diameter approximately 0.5 mm and the extrudate conduit diameter approximately 1.5 mm.

As the molten wax and carrier fluid are pumped through the extruder of the orifice contactor, the two streams come into contact. Since the two streams are immiscible, their differential flow rates result in a serial alternation of wax and carrier segments to be produced (e.g., wax, carrier fluid, wax, carrier fluid, which repeats). The sizes of the wax and carrier segments determine the size and shape of the particle produced. Thus, smaller wax segments from smaller flow rates can produce smaller particles, while larger wax segments from larger flow rates can produce larger particles.

As the molten wax segments enter into the particle collector, the wax being less dense floats within the particle collector, whose top end is maintained at a temperature lower than the melting point of the wax. As the molten wax moves through the fluid column of the particle collector, it begins to solidify and becomes a solid as it reaches the top end that has the lower temperature. The control system can be programmed such that the first set of wax particles that are produced are diverted into the waste chamber, and then at a designated time or upon suitable analysis the wax particles can be diverted to the product collector and the wax particles are collected as products. The wax particles can be in the form of beads that are flowed into the particle collector and product collector, and filtered to retrieve the solid wax beads.

During the protocol, once the desired amount of wax particles is generated, the wax pump and heating is turned off. The heated carrier fluid is continually pumped through the system to remove any residual wax in the system. After approximately 5 minutes of pumping heated carrier fluid, the heater for the carrier fluid reservoir is turned off and the pump for the carrier fluid is turned off.

When needed, a cleaner fluid can be introduced into the wax reservoir and processed through the system to remove wax from the wax reservoir and conduits that convey the molten wax. The cleaner fluid may be miscible with the wax or a known solvent for the wax. In one aspect, the carrier fluid may be drained from the system, such as through a plug in the bottom of the particle collector, or otherwise withdrawn. Then, the cleaner fluid may be used to clean the system. The cleaner fluid may also be introduced into the carrier fluid reservoir and associated conduits. The cleaner fluid may then be removed from the system to remove any wax that is contained or entrained therein.

In one embodiment, the technology described herein can be devoid of unconfined extrusion, that includes an orifice through which the molten fluid (e.g., lipid or wax) is extruded/injected that is substantially smaller than that of the surrounding fluid bath, such as a small pipe opening into a significantly larger reservoir. Instead, the present technology emits the molten fluid through an orifice that has a relative size to a carrier conduit having the carrier fluid, where the size difference is not substantial.

The present process includes confined extrusion where the wax or lipid is extruded and then co-flowed with the carrier fluid in a confined conduit. The relative rate of flow of the wax/lipid compared to the carrier fluid allows for the process to segment the molten wax into a series of droplets within the carrier fluid. Both the orifice dimensions and the flow rates can finely control the size of the droplets. Thus, modulating the orifice dimension relative to the dimension of the conduit having the carrier fluid, and/or modulating the flow rates of the wax or lipid or flow rates of the carrier fluid can result in tuning the system for obtaining particles of a desired size with narrow polydispersity. In confined extrusion, extruded fluid (i.e. wax) is co-flowed within a confined conduit of immiscible fluid. The extruded fluid is broken into segments of droplets that are encased by the immiscible fluid that is larger but only by less than an order of magnitude ($\text{Width}_{orifice} < \text{Width}_{bath}$). The present technology can be considered to be a process that is confined extrusion.

For the processes and methods disclosed herein, the operations performed in the processes and methods may be implemented in differing order. Furthermore, the outlined operations are only provided as examples, and some operations may be optional, combined into fewer operations, eliminated, supplemented with further operations, or expanded into additional operations, without detracting from the essence of the disclosed embodiments.

The present disclosure is not to be limited in terms of the particular embodiments described in this application, which are intended as illustrations of various aspects. Many modifications and variations can be made without departing from its spirit and scope. Functionally equivalent methods and apparatuses within the scope of the disclosure, in addition to those enumerated herein, are possible from the foregoing descriptions. Such modifications and variations are intended to fall within the scope of the appended claims. The present disclosure is to be limited only by the terms of the appended claims, along with the full scope of equivalents to which such claims are entitled. The terminology used herein is for the purpose of describing particular embodiments only, and is not intended to be limiting.

In one embodiment, the present methods can include aspects performed on a computing system. As such, the computing system can include a memory device that has the computer-executable instructions for performing the methods. The computer-executable instructions can be part of a computer program product that includes one or more algorithms for performing any of the methods of any of the claims.

In one embodiment, any of the operations, processes, or methods, described herein can be performed or cause to be performed in response to execution of computer-readable instructions stored on a computer-readable medium and executable by one or more processors. The computer-readable instructions can be executed by a processor of a wide range of computing systems from desktop computing systems, portable computing systems, tablet computing systems, hand-held computing systems, as well as network elements, and/or any other computing device. The computer readable medium is not transitory. The computer readable medium is a physical medium having the computer-readable instructions stored therein so as to be physically readable from the physical medium by the computer/processor.

There are various vehicles by which processes and/or systems and/or other technologies described herein can be effected (e.g., hardware, software, and/or firmware), and that the preferred vehicle may vary with the context in which the processes and/or systems and/or other technologies are deployed. For example, if an implementer determines that speed and accuracy are paramount, the implementer may opt for a mainly hardware and/or firmware vehicle; if flexibility is paramount, the implementer may opt for a mainly software implementation; or, yet again alternatively, the implementer may opt for some combination of hardware, software, and/or firmware.

The various operations described herein can be implemented, individually and/or collectively, by a wide range of hardware, software, firmware, or virtually any combination thereof. In one embodiment, several portions of the subject matter described herein may be implemented via application specific integrated circuits (ASICs), field programmable gate arrays (FPGAs), digital signal processors (DSPs), or other integrated formats. However, some aspects of the embodiments disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and/or firmware are possible in light of this disclosure. In addition, the mechanisms of the subject matter described herein are capable of being distributed as a program product in a variety of forms, and that an illustrative embodiment of the subject matter described herein applies regardless of the particular type of signal bearing medium used to actually carry out the distribution. Examples of a physical signal bearing medium include, but are not limited to, the following: a recordable type medium such as a floppy disk, a hard disk drive, a CD, a DVD, a digital tape, a computer memory, or any other physical medium that is not transitory or a transmission. Examples of physical media having computer-readable instructions omit transitory or transmission type media such as a digital and/or an analog communication medium (e.g., a fiber optic cable, a waveguide, a wired communications link, a wireless communication link, etc.).

It is common to describe devices and/or processes in the fashion set forth herein, and thereafter use engineering practices to integrate such described devices and/or processes into data processing systems. That is, at least a portion of the devices and/or processes described herein can be integrated into a data processing system via a reasonable amount of experimentation. A typical data processing system generally includes one or more of a system unit housing, a video display device, a memory such as volatile and non-volatile memory, processors such as microprocessors and digital signal processors, computational entities such as operating systems, drivers, graphical user interfaces, and applications programs, one or more interaction devices, such as a touch pad or screen, and/or control systems, including feedback loops and control motors (e.g., feedback for sensing position and/or velocity, change in temperature; control motors for moving and/or adjusting components and/or quantities). A typical data processing system may be implemented utilizing any suitable commercially available components, such as those generally found in data computing/communication and/or network computing/communication systems.

Figure 9:
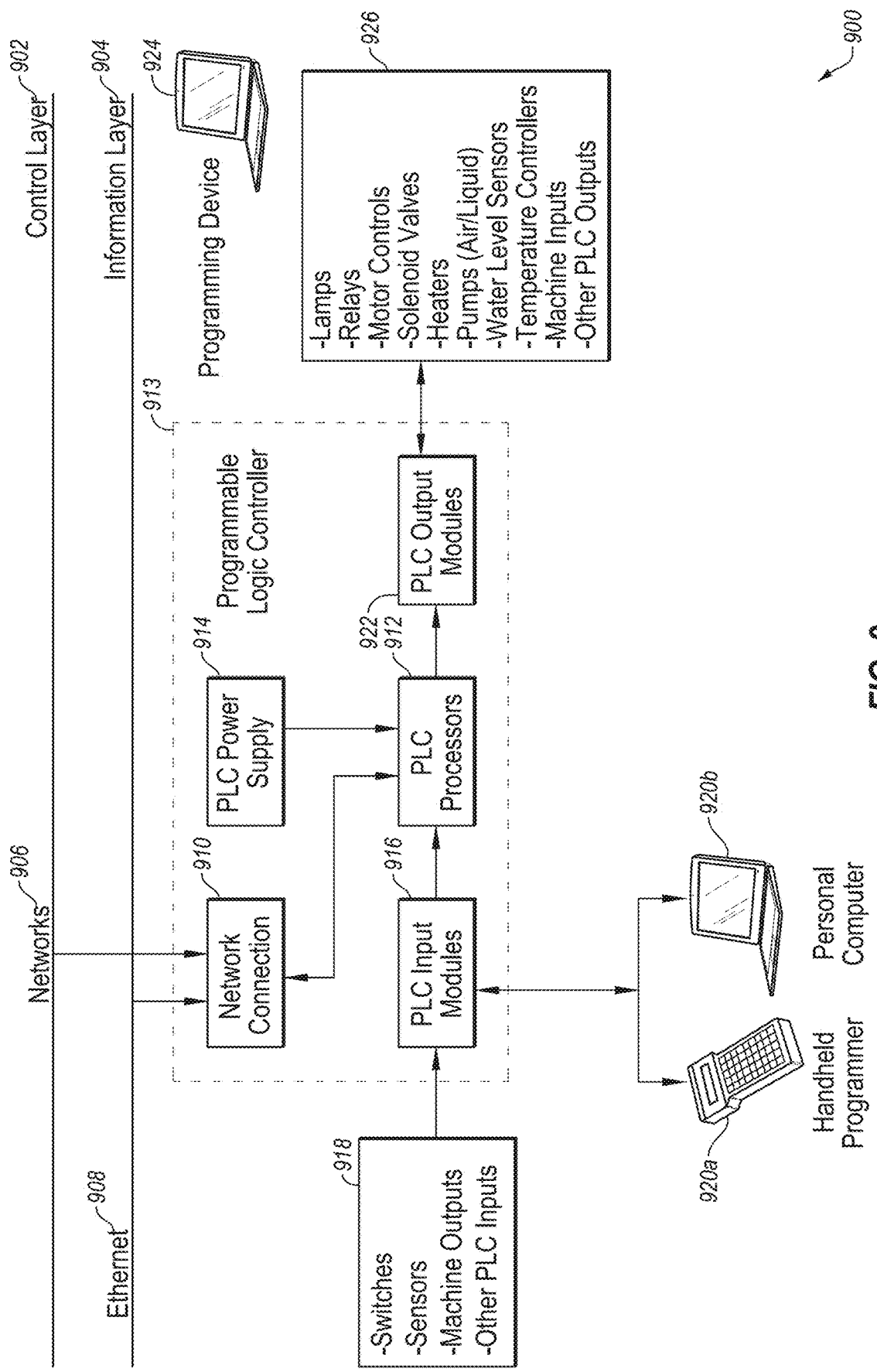
FIG. 9 shows a schematic representation of a control configuration for controlling a particle forming system.

In one embodiment, the system can include programmable logic controllers that can be used to control the entire system of individual components thereof. FIG. 9 shows an example that uses programmable logic controllers. As such, FIG. 9 shows a control configuration 900 that includes a control layer 902 and an information layer 904. The networks 906 and Ethernet 908 are shown, which can communicate with the network connection 910, which can communicate with the programmable logic controller (PLC) processors 912. The PLC processors 912 can be operably coupled with a PLC power supply 914. The PLC input modules 916 receives data from components 918, such as switches, sensors, machine outputs, or other PLC inputs, as well as a user device, such as handheld programmer 920a or personal computer 920b, and provides the data to the PLC processors 912. The PLC processor 912 can provide processed data to the PLC output modules 922. A programming device 924 can be used to interface with the PLC 913. The PLC output modules 922 can provide output to components 926 (e.g., lamps, relays, motor controls, solenoid valves, heaters, pumps (air/liquid), water level sensors, temperature controllers, machine inputs, other PLC outputs). In some instances, the PLC inputs may be configured as PLC outputs, and PLC outputs may be configured as PLC inputs.

In one aspect, programmable logic controller (PLC) 913 can include a PLC power supply operably coupled to the PLC processor, where the PLC processor can be operably coupled with the PLC input modules and operably coupled with the PLC output modules. The PLC input modules can be operably coupled with the different sensors, controllers, and components, such as switches, sensors, machine outputs, and other PLC outputs. The PLC output modules can be operably coupled with components that can be dynamically controlled, such as lamps, relays, motor controllers, solenoid valves, heaters, pumps (e.g., air/liquid), water level sensors, temperature controllers (e.g., heaters and coolers and the controllers thereof), machine inputs, and other PLC inputs. The PLC may also include a tangible (non-transitory) memory device with software or include firmware that can be programmed for one or more operational protocols. The PLC may be operably coupled to a programming device, which can be a computer that includes the computer program to program into the PLC. Also, a handheld programmer or other personal computer can be connected with the PLC, such as through the PLC input modules. The PLC may also include a network connection for making connections and communicating over networks, such as an Ethernet, or the internet. In one example, the Ethernet can provide an information layer, where information regarding the PLC and overall system can be transmitted. In another example, the networks, such as internet or other, may be used for control data to be transmitted. The herein described subject matter sometimes illustrates different components contained within, or connected with, different other components. Such depicted architectures are merely exemplary, and that in fact, many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected", or "operably coupled", to each other to achieve the desired functionality, and any two components capable of being so associated can also be viewed as being "operably couplable", to each other to achieve the desired functionality. Specific examples of operably couplable include, but are not limited to: physically mateable and/or physically interacting components and/or wirelessly interactable and/or wirelessly interacting components and/or logically interacting and/or logically interactable components.

FIG. 6 shows an example computing device 600 that may be arranged in some embodiments to perform the methods (or portions thereof) described herein. This computing device can be used as the system controller described herein. In a very basic configuration 602, computing device 600 generally includes one or more processors 604 and a system memory 606. A memory bus 608 may be used for communicating between processor 604 and system memory 606.

Depending on the desired configuration, processor 604 may be of any type including, but not limited to: a microprocessor (µP), a microcontroller (µC), a digital signal processor (DSP), or any combination thereof. Processor 604 may include one or more levels of caching, such as a level one cache 610 and a level two cache 612, a processor core 614, and registers 616. An example processor core 614 may include an arithmetic logic unit (ALU), a floating point unit (FPU), a digital signal processing core (DSP Core), or any combination thereof. An example memory controller 618 may also be used with processor 604, or in some implementations memory controller 618 may be an internal part of processor 604.

Depending on the desired configuration, system memory 606 may be of any type including, but not limited to: volatile memory (such as RAM), non-volatile memory (such as ROM, flash memory, etc.), or any combination thereof. System memory 606 may include an operating system 620, one or more applications 622, and program data 624. Application 622 may include a determination application 626 that is arranged to perform the operations as described herein, including those described with respect to methods described herein.

Computing device 600 may have additional features or functionality, and additional interfaces to facilitate communications between basic configuration 602 and any required devices and interfaces. For example, a bus/interface controller 630 may be used to facilitate communications between basic configuration 602 and one or more data storage devices 632 via a storage interface bus 634. Data storage devices 632 may be removable storage devices 636, non-removable storage devices 638, or a combination thereof. Examples of removable storage and non-removable storage devices include: magnetic disk devices such as flexible disk drives and hard-disk drives (HDD), optical disk drives such as compact disk (CD) drives or digital versatile disk (DVD) drives, solid state drives (SSD), and tape drives to name a few. Example computer storage media may include: volatile and nonvolatile, removable and non-removable media implemented in any method or technology for storage of information, such as computer readable instructions, data structures, program modules, or other data.

System memory 606, removable storage devices 636 and non-removable storage devices 638 are examples of computer storage media. Computer storage media includes, but is not limited to: RAM, ROM, EEPROM, flash memory or other memory technology, CD-ROM, digital versatile disks (DVD) or other optical storage, magnetic cassettes, magnetic tape, magnetic disk storage or other magnetic storage devices, or any other medium which may be used to store the desired information and which may be accessed by computing device 600. Any such computer storage media may be part of computing device 600.

Computing device 600 may also include an interface bus 640 for facilitating communication from various interface devices (e.g., output devices 642, peripheral interfaces 644, and communication devices 646) to basic configuration 602 via bus/interface controller 630. Example output devices 642 include a graphics processing unit 648 and an audio processing unit 650, which may be configured to communicate to various external devices such as a display or speakers via one or more A/V ports 652. Example peripheral interfaces 644 include a serial interface controller 654 or a parallel interface controller 656, which may be configured to communicate with external devices such as input devices (e.g., keyboard, mouse, pen, voice input device, touch input device, etc.) or other peripheral devices (e.g., printer, scanner, etc.) via one or more I/O ports 658. An example communication device 646 includes a network controller 660, which may be arranged to facilitate communications with one or more other computing devices 662 over a network communication link via one or more communication ports 664.

The network communication link may be one example of a communication media. Communication media may generally be embodied by computer readable instructions, data structures, program modules, or other data in a modulated data signal, such as a carrier wave or other transport mechanism, and may include any information delivery media. A "modulated data signal" may be a signal that has one or more of its characteristics set or changed in such a manner as to encode information in the signal. By way of example, and not limitation, communication media may include wired media such as a wired network or direct-wired connection, and wireless media such as acoustic, radio frequency (RF), microwave, infrared (IR), and other wireless media. The term computer readable media as used herein may include both storage media and communication media.

Computing device 600 may be implemented as a portion of a small-form factor portable (or mobile) electronic device such as a cell phone, a personal data assistant (PDA), a personal media player device, a wireless web-watch device, a personal headset device, an application specific device, or a hybrid device that include any of the above functions. Computing device 600 may also be implemented as a personal computer including both laptop computer and non-laptop computer configurations. The computing device 600 can also be any type of network computing device. The computing device 600 can also be an automated system as described herein.

The embodiments described herein may include the use of a special purpose or general-purpose computer including various computer hardware or software modules.

Embodiments within the scope of the present invention also include computer-readable media for carrying or having computer-executable instructions or data structures stored thereon. Such computer-readable media can be any available media that can be accessed by a general purpose or special purpose computer. By way of example, and not limitation, such computer-readable media can comprise RAM, ROM, EEPROM, CD-ROM or other optical disk storage, magnetic disk storage or other magnetic storage devices, or any other medium which can be used to carry or store desired program code means in the form of computer-executable instructions or data structures and which can be accessed by a general purpose or special purpose computer. When information is transferred or provided over a network or another communications connection (either hardwired, wireless, or a combination of hardwired or wireless) to a computer, the computer properly views the connection as a computer-readable medium. Thus, any such connection is properly termed a computer-readable medium. Combinations of the above should also be included within the scope of computer-readable media.

Computer-executable instructions comprise, for example, instructions and data which cause a general purpose computer, special purpose computer, or special purpose processing device to perform a certain function or group of functions. Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims.

As used herein, the term "module" or "component" can refer to software objects or routines that execute on the computing system. The different components, modules, engines, and services described herein may be implemented as objects or processes that execute on the computing system (e.g., as separate threads). While the system and methods described herein are preferably implemented in software, implementations in hardware or a combination of software and hardware are also possible and contemplated. In this description, a "computing entity" may be any computing system as previously defined herein, or any module or combination of modulates running on a computing system.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," and the like include the number recited and refer to ranges which can be subsequently broken down into subranges as discussed above. Finally, as will be understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

From the foregoing, it will be appreciated that various embodiments of the present disclosure have been described herein for purposes of illustration, and that various modifications may be made without departing from the scope and spirit of the present disclosure. Accordingly, the various embodiments disclosed herein are not intended to be limiting, with the true scope and spirit being indicated by the following claims.

All references recited herein are incorporated herein by specific reference in their entirety, including: U.S. Pat. Nos. 8,883,864; 8,663,511; 8,551,763; 8,114,319; 8,021,582; 3,468,986; 3,389,194; 3,329,994; 3,320,338; and 3,092,553.

The invention claimed is:

1. A system for forming particles, the system comprising:
   a conduit with a conduit lumen having a first cross-sectional dimension and having a conduit inlet and a conduit outlet;
   an extruder tube having an extruder inlet and an extruder orifice as an extruder outlet located within the conduit, the extruder orifice having a second cross-sectional dimension that is smaller than the first cross-sectional dimension;
   a particle collector fluidly coupled with the conduit outlet, wherein the particle collector has a collector inlet, a product collector outlet, and a waste outlet;
   a particle analyzer operatively coupled with the particle collector so as to be capable of analyzing particles within the particle analyzer, wherein the particle analyzer includes a camera;
   a control system having a computer processor adapted to control the system,
      wherein the control system is configured to perform a pre-programmed particle formation protocol comprising:
      flow carrier fluid through the conduit at a pre-programmed flow rate;
      flow extruding material through the extruder orifice at a pre-programmed flow rate into the conduit with the carrier fluid;
      provide the temperature gradient to the particle collector having a preprogrammed first temperature at the collector inlet and a preprogramed temperature at the collector outlet;
      form hardened particles;
      select a waste portion of the hardened particles for waste; and
      select a product portion of the hardened particles for products.

2. The system of claim 1, wherein the control system is operably coupled with the particle analyzer and a particle selector configured for directing particles to the product collector outlet or waste outlet.

3. The system of claim 2, wherein the particle analyzer and control system are configured to:
   analyze the particles; and select particles for waste or for products.

4. The system of claim 1, wherein the particle analyzer is configured to provide a live feed from the camera.

5. The system of claim 4, wherein the particle analyzer and control system are configured to use the live feed from the camera to select defective particles for waste or select product particles for products.

6. The system of claim 2, wherein the control system is configured to receive operational data of measurement components of the system, and provide control instructions to controllable components of the system.

7. The system of claim 6, wherein:
the measurement components are selected from the analyzer, pressure sensor, temperature sensor, flowrate sensor, and combinations thereof; and
the controllable components are selected from heating system, cooling system, pump, material dispenser, carrier fluid dispenser, particle selector, and combinations thereof.

8. The system of claim 6, wherein the control system is configured to modulate operation of one or more controllable components in response to the operational data.

9. The system of claim 1, wherein the pre-programmed particle formation protocol comprises:
a defined startup runtime where all particles are selected for waste; and
a defined product runtime where selected product portion of the particles are for products and selected waste portion of the particles for waste, wherein the product runtime is after the startup runtime.

10. The system of claim 9, wherein the pre-programmed particle formation protocol comprises a defined shutdown runtime where all particles are selected for waste, wherein the shutdown runtime is after the product runtime, wherein during the shutdown runtime the extruder and conduit are cleaned.

11. The system of claim 9, wherein the pre-programmed particle formation protocol comprises:
receive data regarding operation of the system into the control system; and
cause a change in the operation of the system.

12. The system of claim 11, wherein the pre-programmed particle formation protocol comprises:
identify a deviation from the pre-programmed particle formation protocol; and
select all particles formed after the identified deviation for waste.

13. The system of claim 1, further comprising a secondary coolant fluid inlet at a location in the carrier fluid conduit or particle collector.

14. The system of claim 1, wherein the conduit and extruder tube are separate members adapted to be coupled together.

15. A method of forming particles, the method comprising:
providing the system of claim 1;
flowing heated carrier fluid through the conduit at a flowrate;
extruding heated material with the extruder into a carrier fluid that is flowing through the conduit to obtain an extrudate that separates into extrudate segments that are separated from each other by carrier fluid segments;
flowing the extrudate through the particle collector so as to form hardened particles; and
analyzing the particles with the particle analyzer.

16. The method of claim 15, further comprising selecting particles for the product collector outlet or waste outlet based on the analyzing by the particle analyzer.

17. The method of claim 15, further comprising providing a live feed from the camera of the particle analyzer.

18. The method of claim 15, further comprising:
operating the pre-programmed particle formation protocol;
flowing carrier fluid through the conduit at a pre-programmed flow rate;
flowing extruding material through the extruder orifice at a pre-programmed flow rate into the conduit with the carrier fluid;
providing the temperature gradient to the particle collector having a preprogrammed first temperature at the collector inlet and a preprogramed temperature at the collector outlet;
forming hardened particles;
selecting a waste portion of the hardened particles for waste; and
selecting a product portion of the hardened particles for products.

19. The method of claim 18, wherein operating the pre-programmed particle formation protocol comprises:
performing a defined startup runtime where all particles are selected for waste; and
performing a defined product runtime where selected product portion of the particles are for products and selected waste portion of the particles for waste, wherein the product runtime is after the startup runtime.

20. The method of claim 19, wherein the pre-programmed particle formation protocol comprises performing a defined shutdown runtime where all particles are selected for waste, wherein the shutdown runtime is after the product runtime, wherein during the shutdown runtime the extruder and conduit are cleaned.

21. The method of claim 18, wherein the pre-programmed particle formation protocol comprises:
receiving data regarding operation of the system into the control system; and
causing a change in the operation of the system.

22. The method of claim 18, further comprising:
identifying a deviation from the pre-programmed particle formation protocol; and
selecting all particles formed after the identified deviation for waste.

* * * * *